(12) United States Patent
Knodel

(10) Patent No.: US 8,439,246 B1
(45) Date of Patent: May 14, 2013

(54) SURGICAL STAPLER WITH CARTRIDGE-ADJUSTABLE CLAMP GAP

(75) Inventor: Bryan D. Knodel, Flagstaff, AZ (US)

(73) Assignee: Cardica, Inc., Redwood City, CA (US)

( * ) Notice: Subject to any disclaimer, the term of this patent is extended or adjusted under 35 U.S.C. 154(b) by 272 days.

(21) Appl. No.: 12/840,156

(22) Filed: Jul. 20, 2010

(51) Int. Cl.
*A61B 17/068* (2006.01)

(52) U.S. Cl.
USPC .................... 227/180.1; 227/19; 227/176.1

(58) Field of Classification Search ............. 227/19, 227/175.1, 176.1, 178.1, 180.1
See application file for complete search history.

(56) References Cited

U.S. PATENT DOCUMENTS

| | | |
|---|---|---|
| 3,581,551 A | 6/1971 | Wilkinson |
| 3,650,453 A | 3/1972 | Smith, Jr. |
| 3,675,688 A | 7/1972 | Bryan et al. |
| 3,717,294 A | 2/1973 | Green |
| 3,837,555 A | 9/1974 | Green |
| 3,899,914 A | 8/1975 | Akiyama |
| 3,955,581 A | 5/1976 | Spasiano et al. |
| 4,043,504 A | 8/1977 | Hueil et al. |
| 4,086,926 A | 5/1978 | Green et al. |
| 4,127,227 A | 11/1978 | Green |
| 4,228,895 A | 10/1980 | Larkin |
| 4,275,813 A | 6/1981 | Noiles et al. |
| 4,475,679 A | 10/1984 | Fleury, Jr. |
| 4,523,707 A | 6/1985 | Blake, III et al. |
| 4,556,058 A | 12/1985 | Green |
| 4,633,861 A | 1/1987 | Chow et al. |
| 4,655,222 A | 4/1987 | Florez et al. |
| 4,719,917 A | 1/1988 | Barrows et al. |
| 4,762,260 A | 8/1988 | Richards et al. |
| 4,969,591 A | 11/1990 | Richards et al. |
| 4,978,049 A | 12/1990 | Green |
| 5,156,315 A | 10/1992 | Green et al. |
| 5,170,925 A | 12/1992 | Madden et al. |
| 5,192,288 A | 3/1993 | Thompson et al. |
| 5,269,792 A | 12/1993 | Kovac et al. |
| 5,307,976 A | 5/1994 | Olson et al. |

(Continued)

FOREIGN PATENT DOCUMENTS

| | | |
|---|---|---|
| EP | 1238634 | 9/1994 |
| EP | 1464287 | 10/2004 |

(Continued)

OTHER PUBLICATIONS

Gong, Shao W., "Perfectly flexible mechanism and integrated mechanism system design", *Mechanism and Machine Theory 39 (2004)*, (Nov. 2004),1155-1174.

(Continued)

*Primary Examiner* — M. Alexandra Elve
*Assistant Examiner* — Nathaniel Chukwurah
(74) *Attorney, Agent, or Firm* — Cardica, Inc.

(57) ABSTRACT

An exemplary surgical apparatus for treating tissue may include an anvil; a jaw pivotally connected to the anvil; and a first cartridge detachably connected to the anvil, holding staples of a first size; where a first clamp gap between the anvil and first cartridge is set by the connection between the first cartridge and jaw. An exemplary cartridge for a surgical stapler may include a cartridge housing; a plurality of staples held within the cartridge housing; and a sled slidable within, and retained by, the cartridge housing, including a central platform, at least one wedge connected to the central platform, and a knife rotatable relative to the central platform.

13 Claims, 18 Drawing Sheets

U.S. PATENT DOCUMENTS

| | | | |
|---|---|---|---|
| 5,413,272 A | 5/1995 | Green et al. | |
| 5,456,400 A | 10/1995 | Shichman et al. | |
| 5,476,206 A | 12/1995 | Green | |
| 5,527,319 A | 6/1996 | Green et al. | |
| 5,533,521 A * | 7/1996 | Granger | 600/587 |
| 5,547,117 A | 8/1996 | Hamblin et al. | |
| 5,547,474 A | 8/1996 | Kloeckl et al. | |
| 5,553,765 A | 9/1996 | Knodel et al. | |
| 5,620,289 A | 4/1997 | Curry | |
| 5,626,585 A | 5/1997 | Mittelstadt et al. | |
| 5,630,541 A | 5/1997 | Williamson, IV et al. | |
| 5,651,491 A * | 7/1997 | Heaton et al. | 227/175.1 |
| 5,655,698 A | 8/1997 | Yoon | |
| 5,662,260 A | 9/1997 | Yoon | |
| 5,692,668 A | 12/1997 | Schulze et al. | |
| 5,810,855 A | 9/1998 | Rayburn et al. | |
| 5,816,471 A | 10/1998 | Plyley et al. | |
| 5,855,311 A | 1/1999 | Hamblin et al. | |
| 5,871,135 A | 2/1999 | Williamson IV et al. | |
| 5,875,538 A | 3/1999 | Kish et al. | |
| 5,894,979 A | 4/1999 | Powell | |
| 5,918,791 A | 7/1999 | Sorrentino et al. | |
| 5,964,774 A | 10/1999 | McKean et al. | |
| 6,306,149 B1 | 10/2001 | Meade | |
| 6,391,038 B2 | 5/2002 | Vargas et al. | |
| 6,419,682 B1 | 7/2002 | Appleby et al. | |
| 6,592,597 B2 | 7/2003 | Grant et al. | |
| 6,602,252 B2 | 8/2003 | Mollenauer | |
| 6,716,232 B1 * | 4/2004 | Vidal et al. | 606/205 |
| 6,817,508 B1 | 11/2004 | Racenet | |
| 6,843,403 B2 | 1/2005 | Whitman | |
| 7,025,747 B2 | 4/2006 | Smith | |
| 7,055,730 B2 | 6/2006 | Ehrenfels et al. | |
| 7,097,089 B2 | 8/2006 | Marczyk | |
| 7,111,768 B2 | 9/2006 | Cummins et al. | |
| 7,128,253 B2 | 10/2006 | Mastri et al. | |
| 7,140,527 B2 | 11/2006 | Ehrenfels et al. | |
| 7,168,604 B2 | 1/2007 | Milliman et al. | |
| 7,172,104 B2 | 2/2007 | Scirica et al. | |
| 7,179,267 B2 | 2/2007 | Nolan et al. | |
| 7,207,471 B2 | 4/2007 | Heinrich et al. | |
| 7,213,736 B2 | 5/2007 | Wales et al. | |
| 7,225,963 B2 | 6/2007 | Scirica | |
| 7,225,964 B2 | 6/2007 | Mastri et al. | |
| 7,234,624 B2 | 6/2007 | Gresham et al. | |
| 7,238,195 B2 | 7/2007 | Viola | |
| 7,258,262 B2 | 8/2007 | Mastri et al. | |
| 7,308,998 B2 * | 12/2007 | Mastri et al. | 227/176.1 |
| 7,401,720 B1 | 7/2008 | Durrani | |
| 7,434,715 B2 | 10/2008 | Shelton, IV et al. | |
| 7,467,740 B2 | 12/2008 | Shelton, IV et al. | |
| 7,497,865 B2 | 3/2009 | Willis et al. | |
| 7,506,791 B2 | 3/2009 | Omaits et al. | |
| 7,517,356 B2 | 4/2009 | Heinrich | |
| 7,588,177 B2 | 9/2009 | Racenet | |
| 7,604,151 B2 | 10/2009 | Hess et al. | |
| 7,635,073 B2 | 12/2009 | Heinrich | |
| 7,635,373 B2 | 12/2009 | Ortiz | |
| 7,641,432 B2 | 1/2010 | Lat et al. | |
| 7,644,848 B2 | 1/2010 | Swayze et al. | |
| 2003/0120284 A1 | 6/2003 | Palacios et al. | |
| 2003/0236551 A1 | 12/2003 | Peterson | |
| 2004/0199181 A1 * | 10/2004 | Knodel et al. | 606/139 |
| 2005/0184121 A1 | 8/2005 | Heinrich | |
| 2006/0011699 A1 | 1/2006 | Olson et al. | |
| 2006/0041273 A1 | 2/2006 | Ortiz et al. | |
| 2006/0151567 A1 | 7/2006 | Roy | |
| 2006/0253143 A1 | 11/2006 | Edoga et al. | |
| 2007/0027472 A1 | 2/2007 | Hiles et al. | |
| 2007/0034668 A1 | 2/2007 | Holsten et al. | |
| 2007/0073341 A1 | 3/2007 | Smith et al. | |
| 2007/0083234 A1 | 4/2007 | Shelton, IV et al. | |
| 2007/0118163 A1 | 5/2007 | Boudreaux et al. | |
| 2007/0125828 A1 | 6/2007 | Rethy et al. | |
| 2007/0175950 A1 | 8/2007 | Shelton, IV et al. | |
| 2008/0078807 A1 | 4/2008 | Hess et al. | |
| 2008/0272175 A1 | 11/2008 | Holsten et al. | |

FOREIGN PATENT DOCUMENTS

| | | |
|---|---|---|
| EP | 1736104 | 3/2009 |
| JP | 2005160933 | 6/2005 |
| RU | 2080833 | 6/1997 |
| WO | WO-81/01953 | 7/1981 |
| WO | WO-85/01427 | 4/1985 |

OTHER PUBLICATIONS

Lim, Jonas J., et al., "A review of mechanism used in laparascopic surgical instruments", *Mechanism and Machine Theory 38*, (2003),1133-1147.

Lim, Jyue B., "Type Synthesis of a Complex Surgical Device", *Masters Thesis*, (Feb. 21, 2001).

Lim, Jonas J., et al., "Application of Type Synthesis Theory to the Redesign of a Complex Surgical Instrument", *Journal of Biomechanical Engineering (124)*,(Jun. 2004),265-272.

Kolios, Efrossini et al., "Microlaparoscopy", *J. Endourology 18(9)*, (Nov. 2004),811-817.

Steichen, Felicien M., et al., "Mechanical Sutures in Surgery", *Brit. J. Surg. 60 (3)*, (Mar. 1973),191-197.

"Notification of Transmittal of the International Search Report and the Written Opinion of the International Searching Authority", PCT/US2008/075449.

"International Search Report", PCT/US2008/075449.

"Written Opinion of the International Searching Authority", PCT/US2008/075449.

* cited by examiner distal

FIG. 21
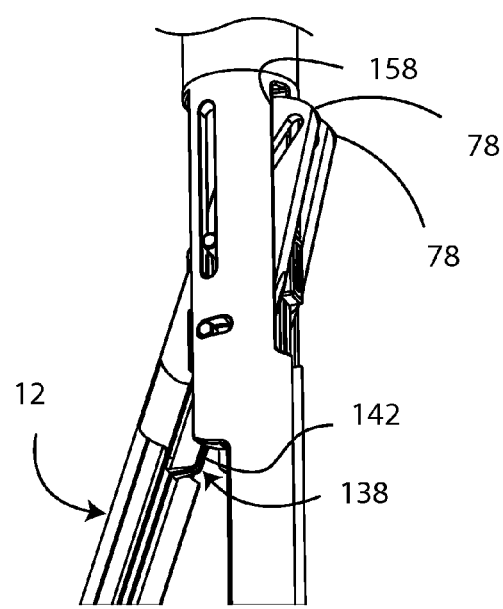
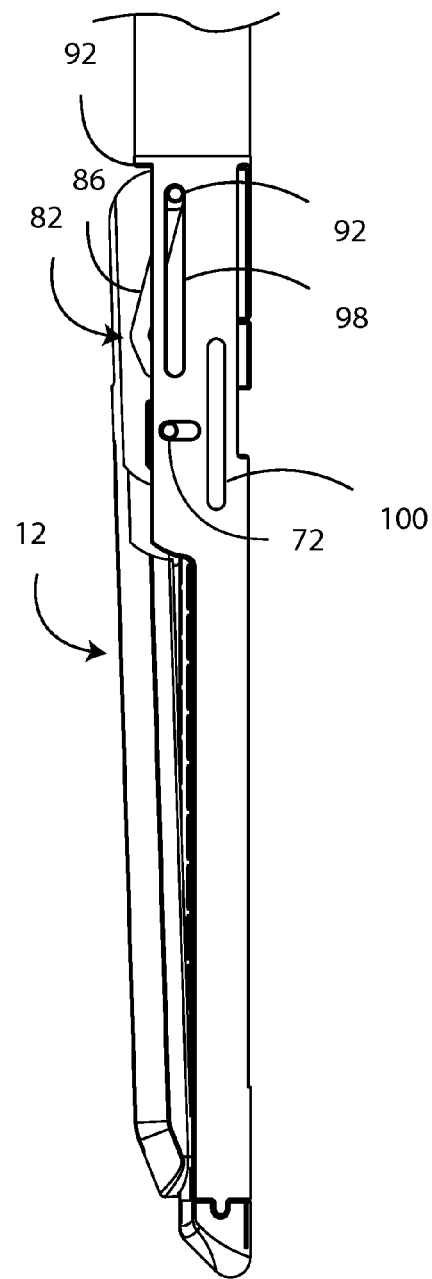
FIG. 22

SURGICAL STAPLER WITH CARTRIDGE-ADJUSTABLE CLAMP GAP

FIELD OF THE INVENTION

The invention generally relates to surgical staplers and stapling.

BACKGROUND

A linear cutter is a surgical tool that staples and cuts tissue to transect that tissue while leaving the cut ends hemostatic. A typical endocutter receives at its distal end a disposable single-use cartridge that holds several rows of staples, and includes an anvil opposed to the cartridge. The cartridge typically includes drivers positioned under the staples. The surgeon orients the end of the endocutter around the tissue to be transected, and compresses the anvil and cartridge together to clamp the tissue. Then, wedges advance into the cartridge, sequentially pushing the drivers upward, and the drivers in turn drive the staples upward against the anvil. Rows of staples are deployed on either side of the transection line, and a blade is advanced along the transection line to divide the tissue. In conventional surgical staplers, it is important to maintain a substantially constant gap between the anvil and the cartridge for proper staple formation. A staple urged outward from the cartridge or other staple holder is designed to encounter a staple pocket or other feature in the anvil at a certain point in its travel. If the staple encounters that staple pocket or other feature in the anvil too soon or too late, the staple may be malformed. For example, if the gap is too large, the staple may not be completely formed. As another example, if the gap is too small, the staple may be crushed. For this reason, a particular conventional linear cutter can only accept a cartridge with a corresponding particular staple size. Inserting into that linear cutter a cartridge holding larger or smaller staples, if that were even possible due to the size differential in the staples and staple drivers, would cause incomplete formation or malformation of those staples.

BRIEF DESCRIPTION OF THE DRAWINGS

FIG. 21 is a lower perspective view of the end effector of FIG. 2 in an open position.

FIG. 22 is a side view of the end effector of FIG. 2 in the clamped position, loaded with a blue cartridge of FIG. 5.

The use of the same reference symbols in different figures indicates similar or identical items.

DETAILED DESCRIPTION

U.S. Patent Application Publication No. 2009/0065552, published on Mar. 12, 2009 (the "Endocutter Document"), is hereby incorporated by reference herein in its entirety.

Figure 1:
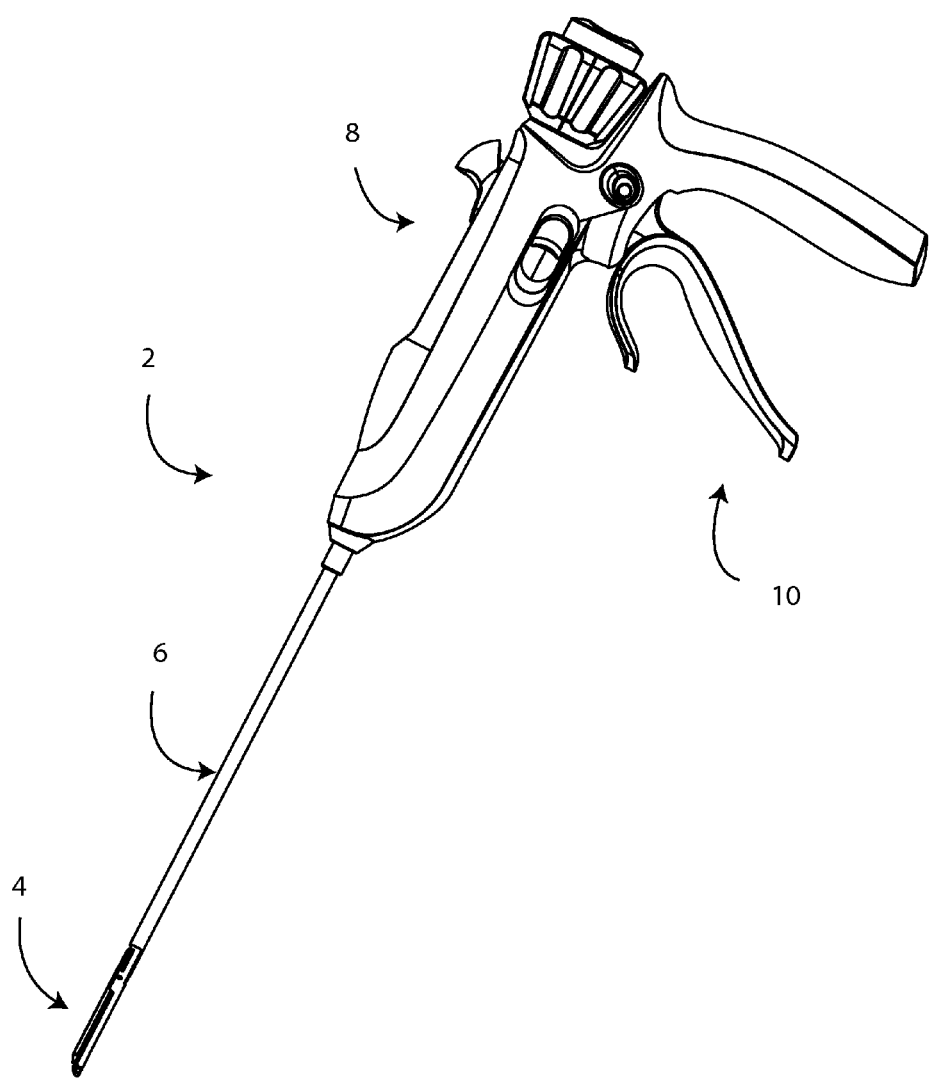
FIG. 1 is a side view of an exemplary surgical stapler.
Figure 2:
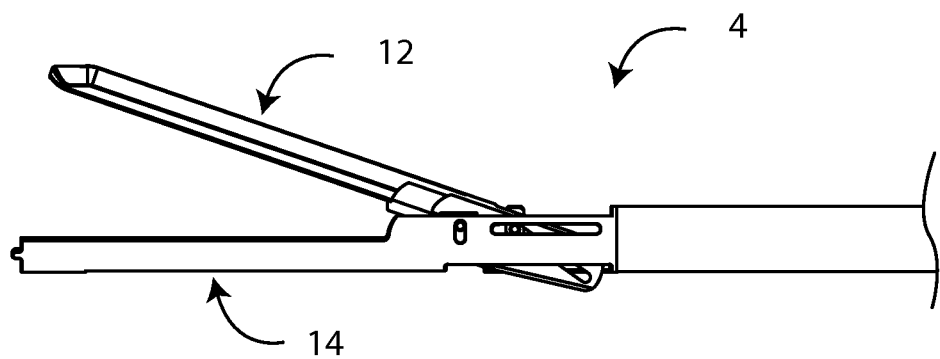
FIG. 2 is a side view of an exemplary end effector of the stapler of FIG. 1, without a cartridge.
Figure 3:
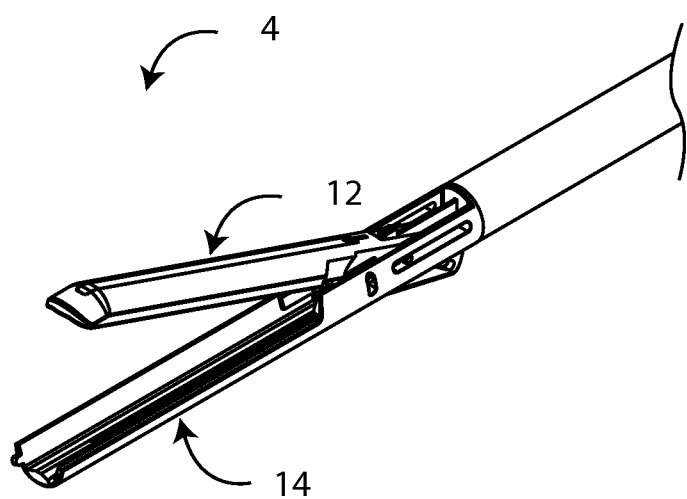
FIG. 3 is a perspective view of the end effector of FIG. 2.
Figure 4:
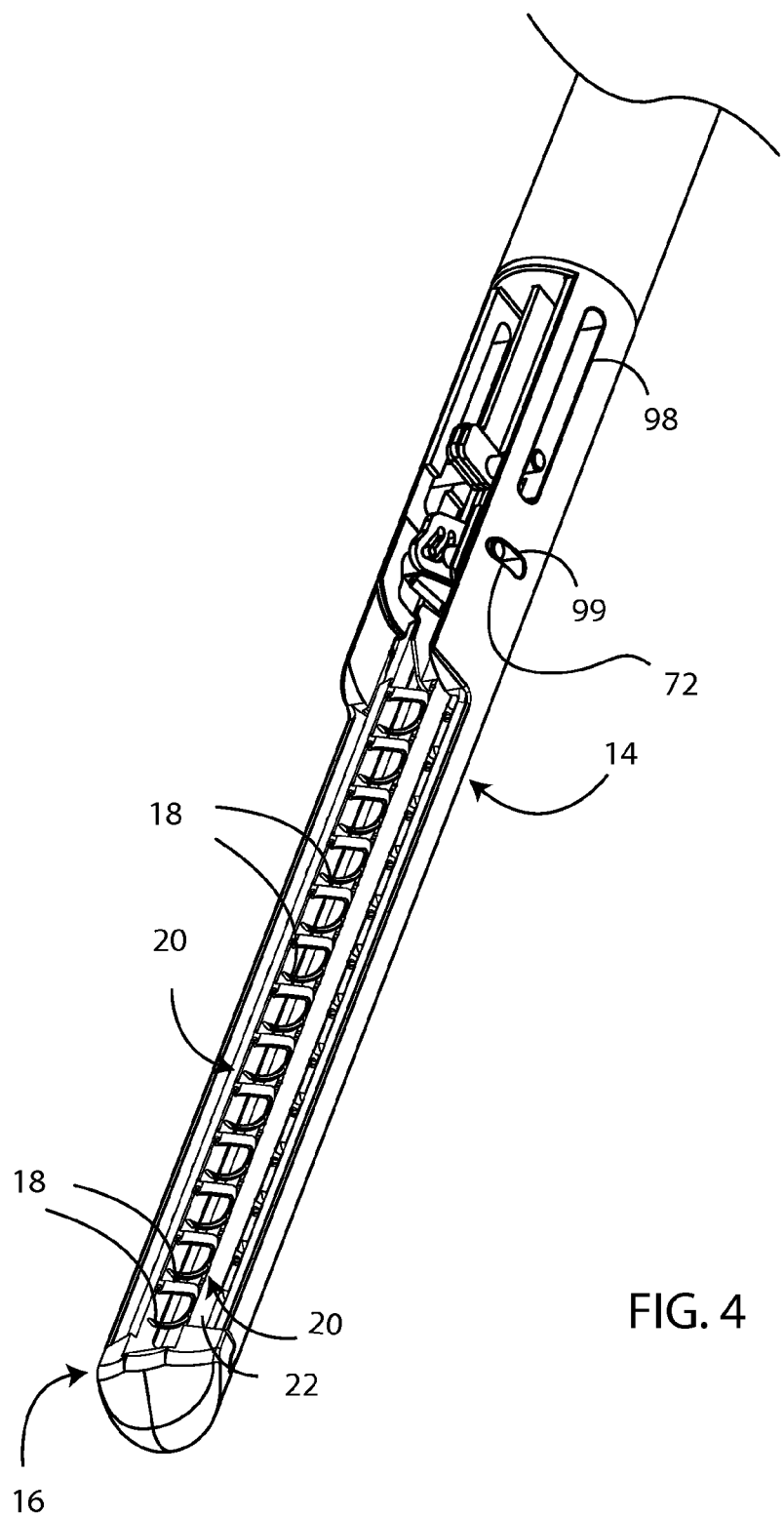
FIG. 4 is a perspective cutaway view of the end effector of FIG. 2, loaded with a blue cartridge.
Figure 5:
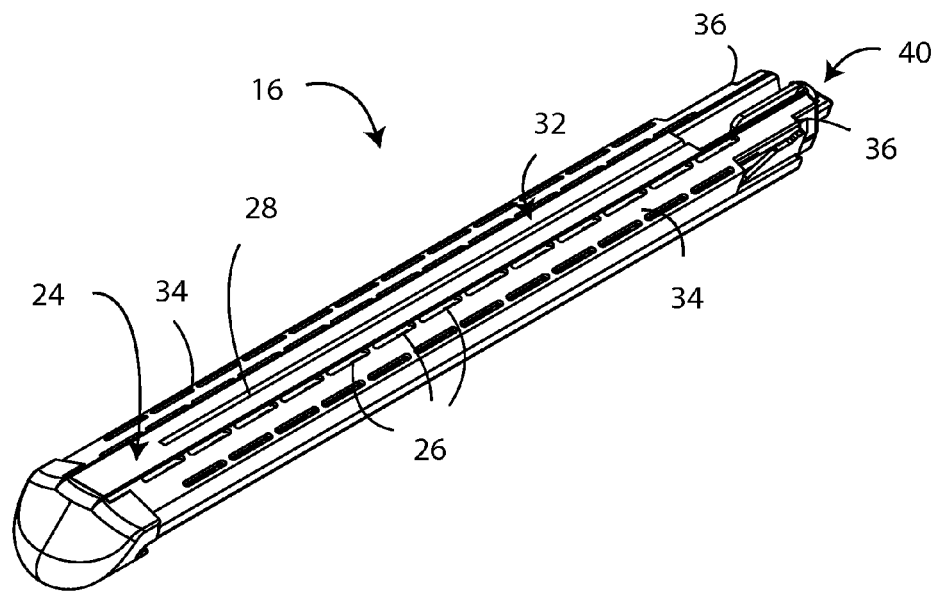
FIG. 5 is a perspective view of an exemplary blue cartridge.
Figure 6:
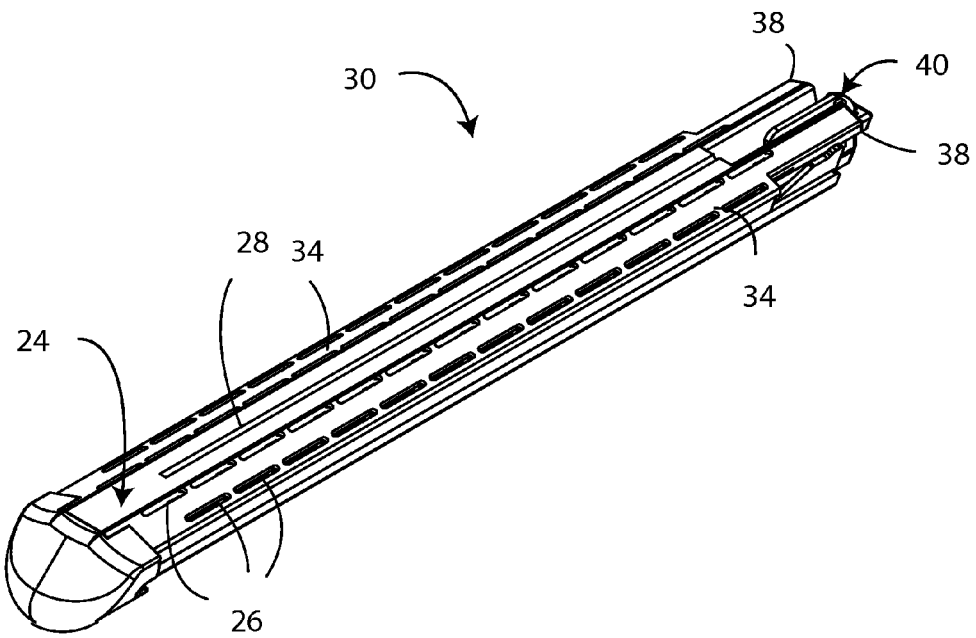
FIG. 6 is a perspective view of an exemplary white cartridge.

Referring to FIG. 1, an exemplary surgical stapler 2 may include an end effector 4 connected to the distal end of a shaft 6. The proximal end of the shaft 6 may in turn be connected to a handle 8. The handle 8 may include a single trigger 10. The shaft 6 may be rigid or articulated. If the shaft 6 is articulated, any articulated region may be exposed, or may be covered with a sleeve or other suitable structure. Referring also to FIGS. 2-3, the end effector 4 may include an anvil 12 and a jaw 14. Referring also to FIGS. 4-6, the jaw 14 may be configured to receive at least one of a blue cartridge 16 and a white cartridge 30. The term "blue cartridge" is standard terminology for a cartridge that fires staples across a 0.035 inch clamp gap, and the term "white cartridge" is standard terminology for a cartridge that fires staples across a 0.020 inch clamp gap. Advantageously, the jaw 14 is configured to receive either cartridge 16, 30, as described in greater detail below. Alternately, the jaw 14 may be configured to receive one or more cartridges having staples of any suitable size.

Referring to FIG. 4, an exemplary blue cartridge 16 is shown, loaded onto the jaw 14. The blue cartridge 16 holds a plurality of staples 18, each frangibly affixed at one end to a corresponding feeder belt 20. The shape of the staples 18, the configuration of the staples 18 and the feeder belt 20, and the attachment between the staples 18 and the feeder belt 20 may be substantially as described in the Endocutter Document. Unlike the feeder belt described in the Endocutter Document, the feeder belt 20 of the blue cartridge 16 may be fixed in position relative to the blue cartridge 16. For example, the blue cartridge 16 may include one or more rails 22 defined therein, where a feeder belt 20 may be affixed to the upper surface of each rail 22. In this way, the blue cartridge 16 may be a single-use cartridge, which is replaced after each firing. The upper surface 24 of the blue cartridge 16 may include a plurality of apertures 26 defined therethrough, positioned in a way that corresponds to the locations of the staples 18 within the blue cartridge 16. Additionally, the upper surface 24 of the blue cartridge 16 may include a knife slot 28 through which a knife may slide, as described in greater detail below. Two rows of apertures 26 may be positioned on each lateral side of the knife slot 28, allowing two rows of staples 18 to be deployed therethrough into tissue, as described in greater detail below. As another example, only a single row of apertures 26 may be provided on at least one lateral side of the knife slot 28, allowing a single row of staples 18 to be deployed therethrough. As another example, three or more rows of apertures 26 may be provided on at least one lateral side of the knife slot 28, allowing three or more rows of staples 18 to be deployed therethrough. The blue cartridge 16 may include a housing 21 that defines a space therein. The upper surface 24 of the blue cartridge 16 may have a generally flat region 32 longitudinally extending along its lateral center, through which the knife slot 28 is defined, and two angled regions 34 connected to and each extending laterally from the generally flat region 32. The apertures 26 may be defined through the angled surfaces 34. The rails 22 defined within the blue cartridge 16 may be angled within the blue cartridge 16 in such a manner that the rails 22 are substantially perpendicular to the angled regions 34. Alternately, the rails 22 may be angled or oriented in any other suitable manner. As another example, the upper surface 24 of the blue cartridge 16 need not include angled regions 34, and instead may be substantially flat along its entirety. As another example of a blue cartridge 16, at least one feeder belt 20 may be configured to advance between firings, in a manner such as set forth in co-pending and commonly-assigned U.S. patent application Ser. No. 12/471,672, filed on May 26, 2009, which is hereby incorporated by reference in its entirety. As another example of a blue cartridge 16, at least one feeder belt 20 may be omitted, and staples 18 that would otherwise have been frangibly affixed to that feeder belt 20 may instead be frangibly affixed to the upper surface 24, each adjacent to a corresponding aperture 26, in a manner such as set forth in co-pending and commonly-assigned U.S. patent application Ser. No. 12/683,382, filed on Jan. 6, 2010, which is hereby incorporated by reference in its entirety.

The white cartridge 30 may be configured in substantially the same way as the blue cartridge 16 described above, with three primary exceptions. First, the white cartridge 30 holds smaller staples 18 than are held by the blue cartridge 16. Second, as a consequence, the white cartridge 30 optionally may be shorter than the blue cartridge 16, although the cartridges 16, 30 may have substantially the same longitudinal dimensions as one another. Third, each cartridge 16, 30 includes a gap-setting feature that engages with the jaw 14 to set the gap between the anvil 12 and the cartridge 16, 30, and that gap-setting feature is located at a different location on each cartridge 16, 30. Referring to FIG. 5, on the blue cartridge 16, the blue gap-setting feature 36 may be located on one or both lateral sides of the blue cartridge 16, near the proximal end of the blue cartridge 16. The blue gap-setting feature 36 may be an indentation inward toward the lateral center of the blue cartridge 16, where a portion of the lateral edge of the blue cartridge 16 immediately proximal to the blue gap-setting feature 36 is located laterally inward relative to a portion of the lateral edge of the white cartridge 30 located immediately distal to the blue gap-setting feature 36. The blue gap-setting feature 36 may be defined on or near the upper surface 24 of the blue cartridge 16, but may be positioned differently on the blue cartridge 16. The interaction between the blue gap-setting feature 36 and the jaw 14 that sets the tissue gap is described in greater detail below. Referring to FIG. 6, on the white cartridge 30, the white gap-setting feature 38 may be located on one or both lateral sides of the white cartridge 30, at the proximal end of the white cartridge 30. The white gap-setting feature 38 may be located more proximal on the white cartridge 30 than the blue gap-setting feature 36 is located on the blue cartridge 16, where that difference in longitudinal position differentially engages the jaw 14 to change the tissue gap between the cartridge 16, 30 and the jaw 14 depending on the cartridge 16, 30 loaded onto the jaw 14. The white gap-setting feature 38 may be an absence of an indentation, particularly where the white gap-setting feature 38 is located at the proximal end of the white cartridge 30, or extends slightly proximal from the proximal end of the white cartridge 30. The white gap-setting feature 38 may be defined on or near the upper surface 24 of the white cartridge 30, but may be positioned differently on the white cartridge 30. The interaction between the white gap-setting feature 38 and the jaw 14 that sets the tissue gap is described in greater detail below. Although a blue cartridge 16 and a white cartridge 30 have been described here, other or additional sizes of cartridge may be fabricated as disclosed above, where differences between the gap-setting features of the cartridges results in a difference in tissue gap between the jaw 14 and the cartridge.

Figure 7:
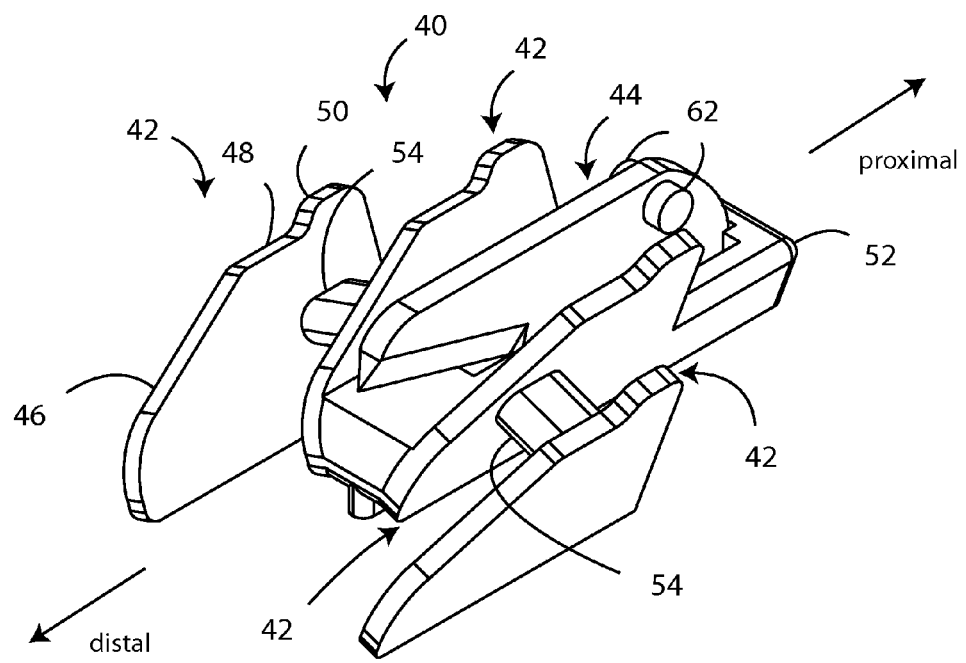
FIG. 7 is a perspective view of an exemplary sled assembly, with a knife in the down position.

Referring to FIG. 7, a sled 40 is slidable along either cartridge 16, 30. The sled 40 may include a plurality of wedges 42, and a knife 44 that may be pivotable relative to a remainder of the sled 40. Each wedge 42 may be shaped in any suitable manner that causes staples 18 contacted by that wedge 42 to first move upward and deform against the anvil 12, then break apart from the feeder belt 20, in a manner such as described in the Endocutter Document. As one example, the upper surface of at least one wedge 42 may include a first surface 46 that may be angled or curved, or both, downwardly in the distal direction. The wedge 42 optionally may also include a second surface 48 proximal to the first surface 46, where the second surface may be substantially flat. Alternately, the second surface 48 is curved or angled, and/or is included as a portion of the first surface. The wedge 42 may include a third surface 50 that may be angled or curved, or both, downwardly in the distal direction. As described in greater detail below, contact between the first surface 46 and a staple 18 bends the staple 18, and contact between the second surface 50 and the staple 18 breaks off the staple 18 from the feeder belt 20. The lower surface of the wedge 42 may be substantially linear.

The wedges 42 may be angled relative to a vertical reference plane defined to pass through both the longitudinal centerline of the cartridge 16, 20 and the knife slot 28 of the cartridge 16, 30. This definition of "vertical," and the use of terms such as "vertical," "horizontal," "lateral," "up,", "down," "upper," and "lower," is solely for convenience in describing the surgical stapler 2, and does not limit the orientation of the surgical stapler 2 in use. The wedges 42 may be angled relative to the reference plane such that the lower surface of each wedge 42 is laterally closer to the reference plane than the upper surface of each wedge 42. The wedges 42 on each side of the reference plane may be substantially parallel to one another, or may be angled relative to each other as well. The sled 40 may include a central platform 52 that is oriented generally longitudinally. Two wedges 42 may be attached directly to the central platform 52, one on each lateral side thereof. An outrigger 54 may extend outward from each of those wedges 42, where each outrigger 54 is in turn connected to a different, further-lateral wedge 42. The central platform 52, wedges 42 and outriggers 54 may be fabricated as an integral unit, such as by molding, or may be fabricated separately and assembled together at a later time. The central platform 52 may include a fin 66 extending from the proximal end thereof. The fin 66 may extend laterally across less than all of the width of the central platform 52, and may be angled such that the bottom of the fin 66 is positioned proximally outward further from the central platform 52 than the top of the fin 66. Alternately, the fin 66 may be omitted, or may extend laterally across the entirety of the proximal end of the central platform 52.

The knife 44 may be received in, and rotatable relative to, the central platform 52. Advantageously, the knife 44 may be substantially laterally centered in the central platform 52, such that the knife 44 is substantially bisected by the reference plane. Referring also to FIG. 9, the central platform 52 may include a knife aperture 56 defined therein. At least part of the knife aperture 56 may extend completely through the central platform 52. A pivot axle 58 may extend laterally from the knife 44; the axle 58 may be a single rod, or may be defined by two separate pins extending from the knife 44. The pivot axle 58 may be received in an axle receiver 60 defined in the central platform 52, which may be part of the knife aperture 56 or separate from the knife aperture 56. The pivot axle 58 may be held by the axle receiver 60 in any way that allows the pivot axle 58 to pivot. The axle receiver 60 may hold the pivot axle 58 laterally and/or longitudinally in a fixed location relative to the central platform 52. One or more flip pins 62 also may extend laterally from the knife 44. The flip pins 62 may be two ends of a single rod, or two separate pins extending from the knife 44. As described in greater detail below, the flip pins 62 are used to flip the knife 44 upward from the initial stowed configuration. As seen in FIGS. 7-10, the knife 44 may be initially configured in a stowed position. In the stowed position, the blade 64 is oriented generally downward, such that a user cannot injure himself or herself due to inadvertent contact with the blade 64.

Figure 9:
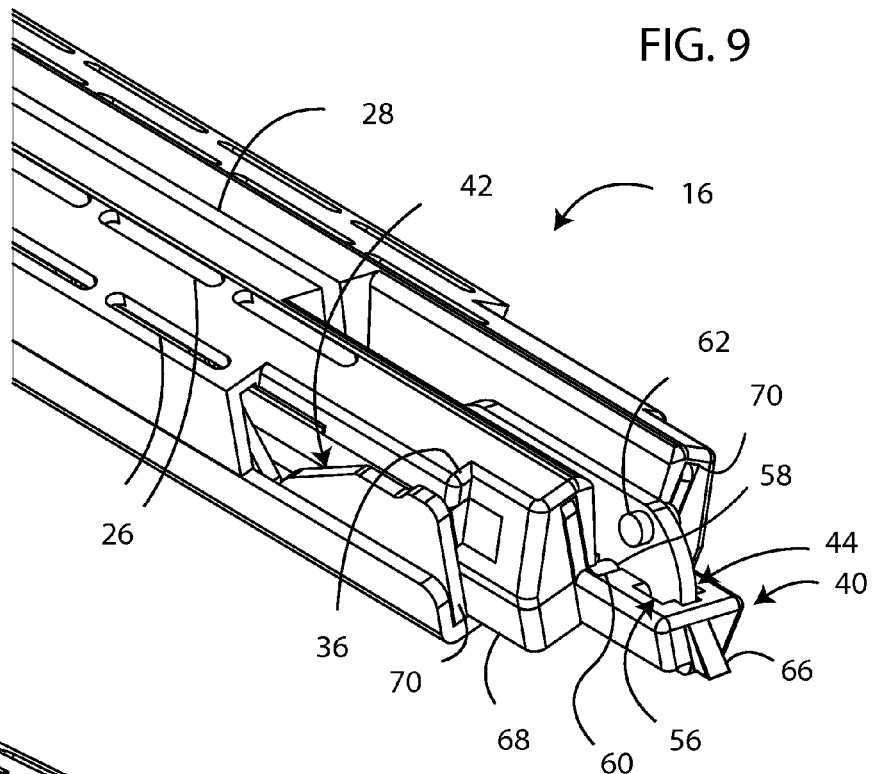
FIG. 9 is a perspective view of the sled assembly of FIGS. 7-8 in an initial position in the blue cartridge of FIG. 5.
Figure 10:
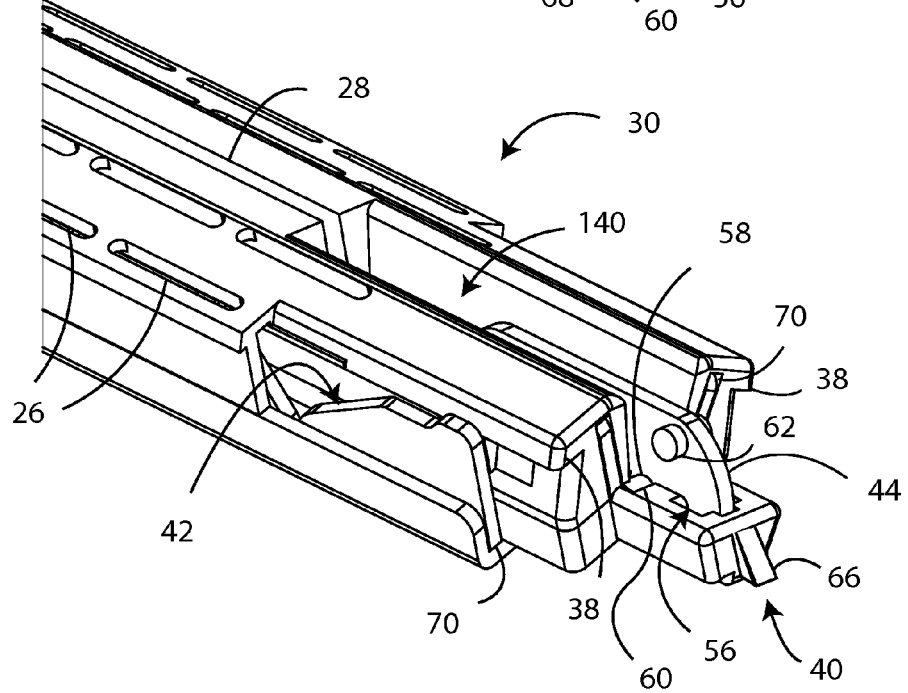
FIG. 10 is a perspective view of the sled assembly of FIGS. 7-8 in an initial position in the white cartridge of FIG. 6.

Referring to FIGS. 9-10, the sled 40 is configured to slide within a remainder of a corresponding cartridge 16, 30. The sled 40 is part of the cartridge 16, 30, such that after depletion of the staples 18 in the cartridge 16, 30, the sled 40 is removed from the jaw 14 with the cartridge 16, 30. In this way, the blade 64 of the knife 44 can retain sharpness effectively; in addition, reloading a fresh cartridge 16, 30 onto the jaw 14 may be simplified by retaining the sled 40 with the remainder of the cartridge 16, 30. The sled 40 may be held within a remainder of the cartridge 16, 30 by at least one outrigger 54, such that the outrigger 54 can only move proximally to a point where it contacts the outer shell 68 of the cartridge 16, 30. The sled 40 is located at that most-proximal point in FIGS. 9-10. Alternately, the sled 40 may be slidable out of the cartridge 16, 30 prior to exchange of the cartridge 16, 30, such that the sled 40 and knife 44 can be reused with different cartridges 16, 30. Each cartridge 16, 30 may include a plurality of slots 70 along which the wedges 42 slide, and which guide the wedges 42 to ensure they slide longitudinally along a substantially linear path to sequentially engage a plurality of staples 18.

Figure 11:
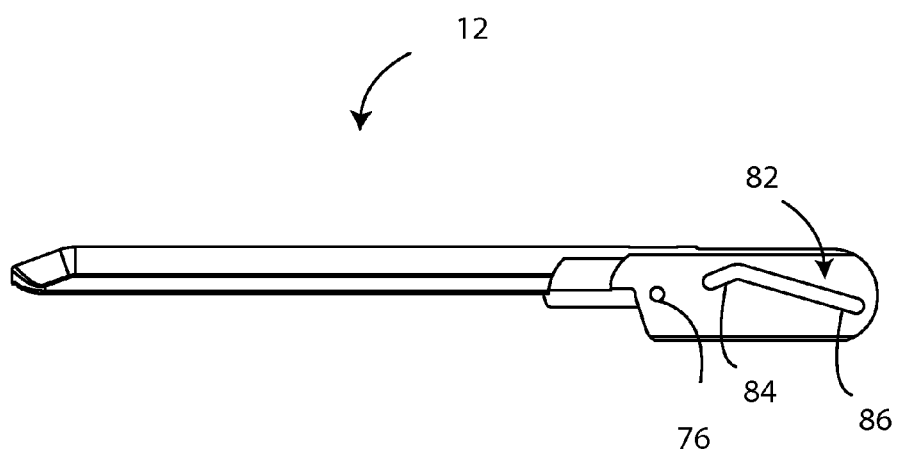
FIG. 11 is a side view of an exemplary anvil.
Figure 12:
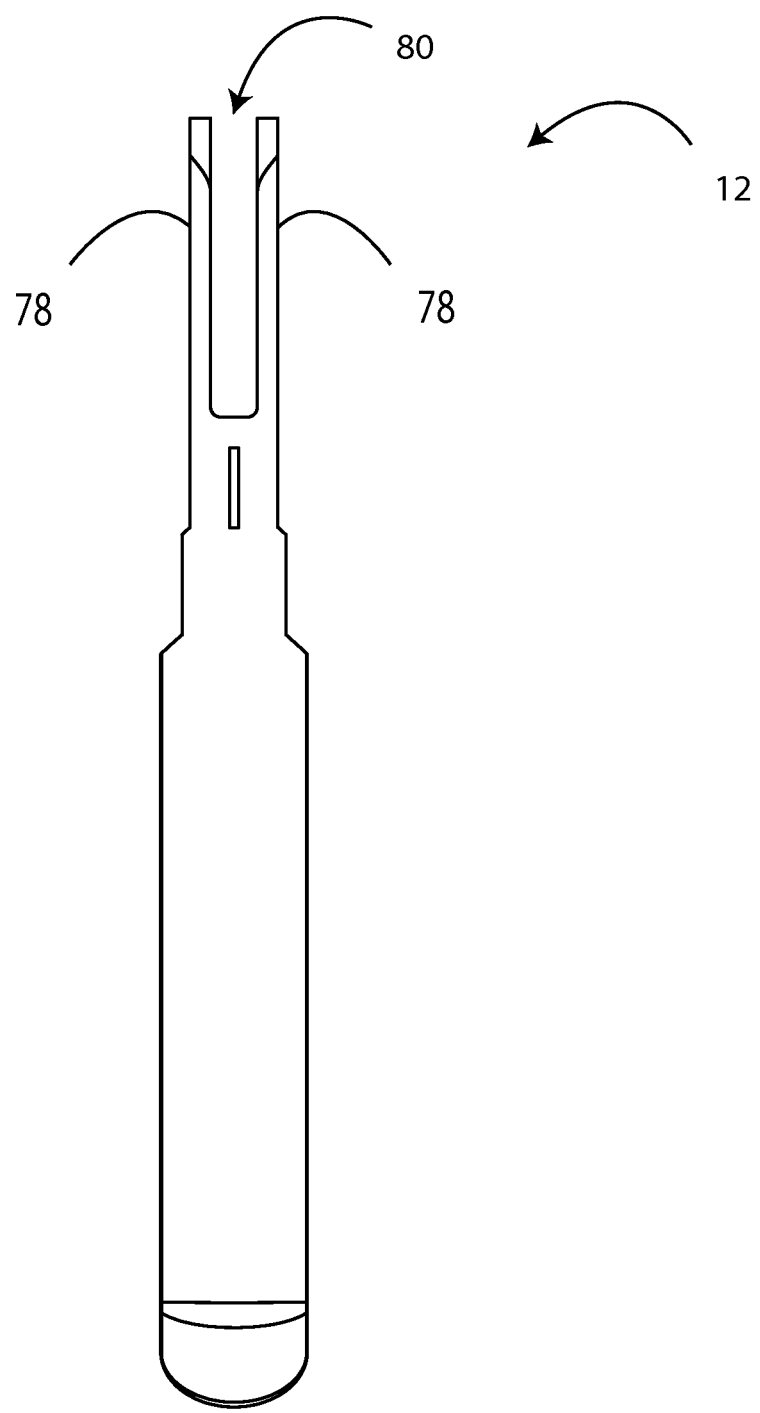
FIG. 12 is a top view of the anvil of FIG. 11.
Figure 13:
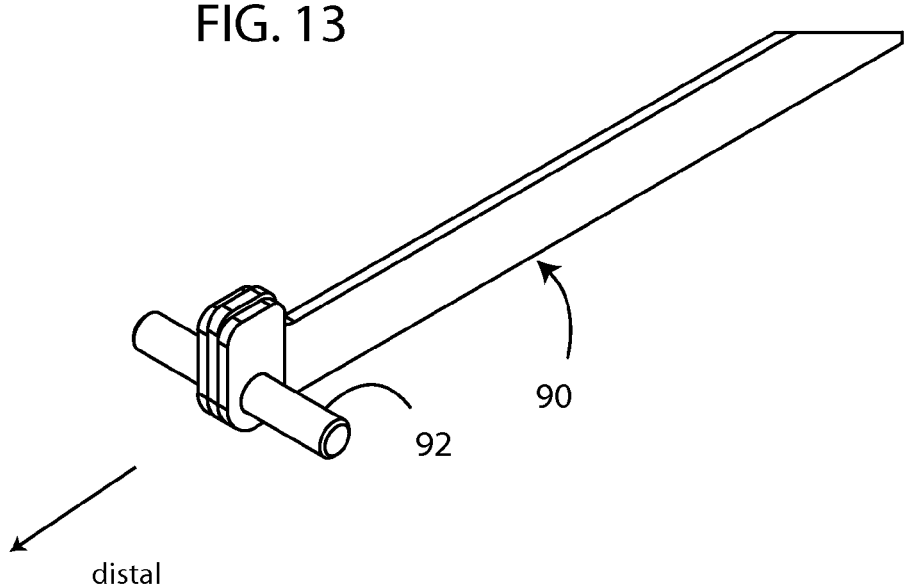
FIG. 13 is a perspective view of an exemplary clamp strip.
Figure 14:
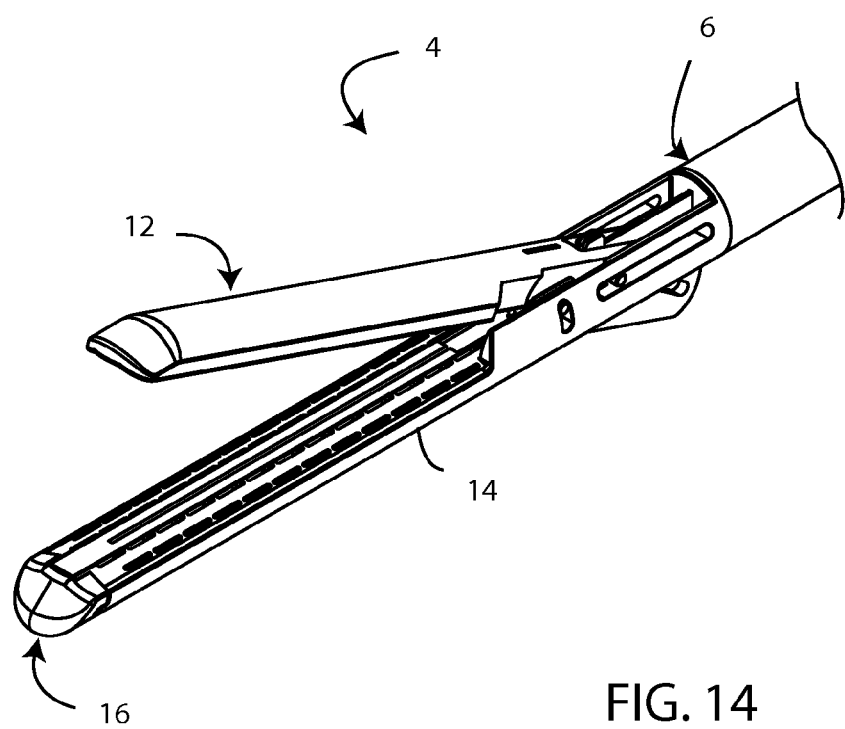
FIG. 14 is a perspective view of the end effector of FIG. 2, loaded with a blue cartridge of FIG. 5.
Figure 15:
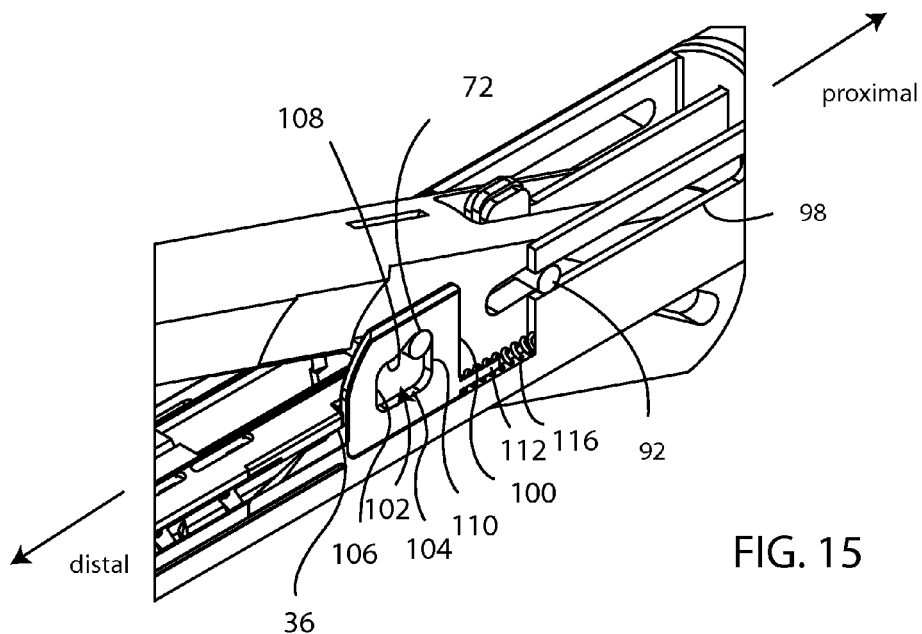
FIG. 15 is a detail cutaway perspective view of the end effector of FIG. 14.

Turning to FIGS. 2 and 11-15, a remainder of the end effector 4 includes the anvil 12 and the jaw 14. The anvil 12 and the jaw 14 may be pivotally interconnected by two pivot pins 72. The pivot pins 72 may be laterally spaced relative to one another, such that the I-beam, described in greater detail below, is able to advance between them. Alternately, a single pivot pin 72 laterally spanning the end effector may be utilized. Referring to FIG. 11, each side of the anvil 12 may include a pivot pin receiver 76 defined therein or completely therethrough, in order to receive the corresponding pivot pin 72 therein. In this way, the anvil 12 is pivotable about the lateral axis defined by the pivot pin receiver 76. The pivot pins 72, and thus the lateral axis defined by the pivot pin receiver 76, may be substantially perpendicular to and spaced apart from the longitudinal centerline of the cartridge 16. Alternately, the pivot pins 72 and pivot pin receiver 76 may be oriented differently relative to one another, and/or the lateral axis defined by the pivot pin receiver 76 may intersect the longitudinal centerline of the cartridge 16. Referring also to FIG. 12, the anvil 12 may include two spaced-apart legs 78 defining a space 80 therebetween. A cam path 82 may be defined in, or completely through, one or both legs 78. The cam path 82 may be configured in any suitable manner. As one example, the cam path 82 includes a first segment 84 and a second segment 86 proximal to the first segment 84, where the segments 84, 86 collectively define a continuous cam path 82. Starting at the distal end of the cam path 82, the first segment 84 defines a path that moves upward in the proximal direction. The first segment 84 may be straight, curved, or both in combination, or otherwise shaped. The second segment 86 then defines a path that moves downward in the proximal direction. The second segment 86 may be straight, curved, or both in combination, or otherwise shaped. Turning to FIG. 13, a clamp strip 90 may include a cam pin 92 attached thereto. The clamp strip 90 may be a thin, elongated structure that is fabricated from metal or any other suitable material. The clamp strip 90 may extend through the shaft 6 to the handle 8 of the surgical stapler 2. The cam pin 92 may be positioned at or near the distal end of the clamp strip 90, and may be oriented generally perpendicular to the longitudinal centerline of the clamp strip 90. Alternately, the cam pin 92 may be oriented differently relative to the clamp strip 90. The cam pin 92 may be a single pin structure, or may be composed of two separate pins, one extending from either lateral side of the clamp strip 90. If so, the two separate pins are advantageously aligned with one another, but need not be. Referring also to FIGS. 14-15, the cam pin 92 is configured to be received in each cam path 82 of the anvil 12. The space 80 defined between the legs 78 of the anvil 12 receives the distal end of the clamp strip 90.

Figure 16:
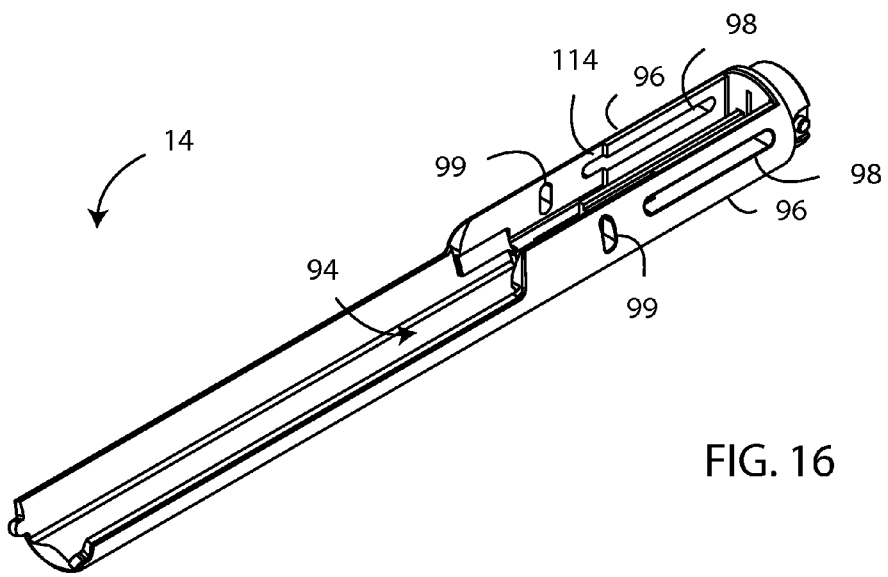
FIG. 16 is a perspective view of an exemplary jaw of the end effector of FIG. 2.

Referring to FIGS. 14-16, the jaw 14 may include a channel 94 defined generally longitudinally along a majority of its length, in its lower, inner surface. At the proximal end of the jaw 14, two jaw walls 96 may be laterally spaced apart by the channel 95. Each jaw wall 96 may include a cam pin slot 98 defined therein or completely therethrough. Each cam pin slot 98 may be substantially straight and substantially parallel to the longitudinal centerline of the jaw 14. Alternately, at least one cam pin slot 98 may be oriented differently. The cam pin slots 98 receive the cam pin 92. Moving from the center laterally outward toward one side, the cam pin 92 extends from the clamp strip 90, then through the cam slot 82 on the leg 78 of the anvil 12, then through the cam pin slot 98 in the jaw wall 96. This interaction between the cam pin 92, the cam slot 82, and the cam pin slot 98 is used to lock the height of the anvil 12 relative to the jaw 14, as described below. Additionally, in each jaw wall 96, a pivot pin slot 99 is defined therein or completely therethrough. The pivot pin slots 99 may be substantially vertical, and each may be substantially perpendicular to the cam pin slot 98 defined in the same jaw wall 96.

Each pivot pin slot 99 is advantageously located distal to and spaced apart from the corresponding cam pin slot 98 in the same jaw wall 96. Alternately, the pivot pin slots 99 may be located or oriented in any other suitable manner. The pivot pin slots 99 receive the pivot pins 72.

Referring to FIG. 15, a shuttle 100 is positioned against at least one jaw wall 96. Advantageously, two shuttles 100 are provided, each associated with a different jaw wall 96. The shuttle 100 includes a center aperture 102 that may be generally trapezoidal. The center aperture 102 may include a lower surface 104, a distal surface 106, an upper surface 108, and a proximal surface 110. The surfaces 104, 106, 108, 110 are generally linear, and curve where they intersect. However, the surfaces 104, 106, 108, 110 may be shaped differently and/or may intersect differently. The lower surface 104 may be generally straight and extend generally longitudinally. The distal surface 106 may be generally straight, and extend generally vertically and generally perpendicular to the lower surface 104. The upper surface 108 may be generally straight, and may be vertically higher at its proximal end than its distal end. Thus, the proximal end of the upper surface 108 may be positioned further away from the lower surface 104 than the distal end of the upper surface 108. The proximal surface 110 may be generally straight, and extend generally vertically and generally perpendicular to the lower surface 104. Advantageously, the proximal surface 110 is longer than the distal surface 106. Each shuttle 110 may be positioned against a shuttle cutout 114 defined in the inner surface of a corresponding jaw wall 96. Each shuttle 100 may include a tail 112 extending in the proximal direction within a tail retainer 116 defined in an inner surface of a corresponding jaw wall 96. Each shuttle 100 may be biased distally, such as by a compression spring wound about a corresponding tail 112. Forward motion of the shuttle 100 as a result of the biasing force of the spring 118 may be limited by the distal end of the corresponding shuttle cutout 114.

Each pivot pin 72 extends into the center aperture 102 of the corresponding shuttle 100. Moving from the center laterally outward toward one side, the pivot pin 72 extends from the deployment strip 74, then through the pivot pin receiver 76 in the anvil 12, then through the center aperture 102 of the shuttle 100, then through the pivot pin slot 99 in the jaw wall 96.

Figure 17:
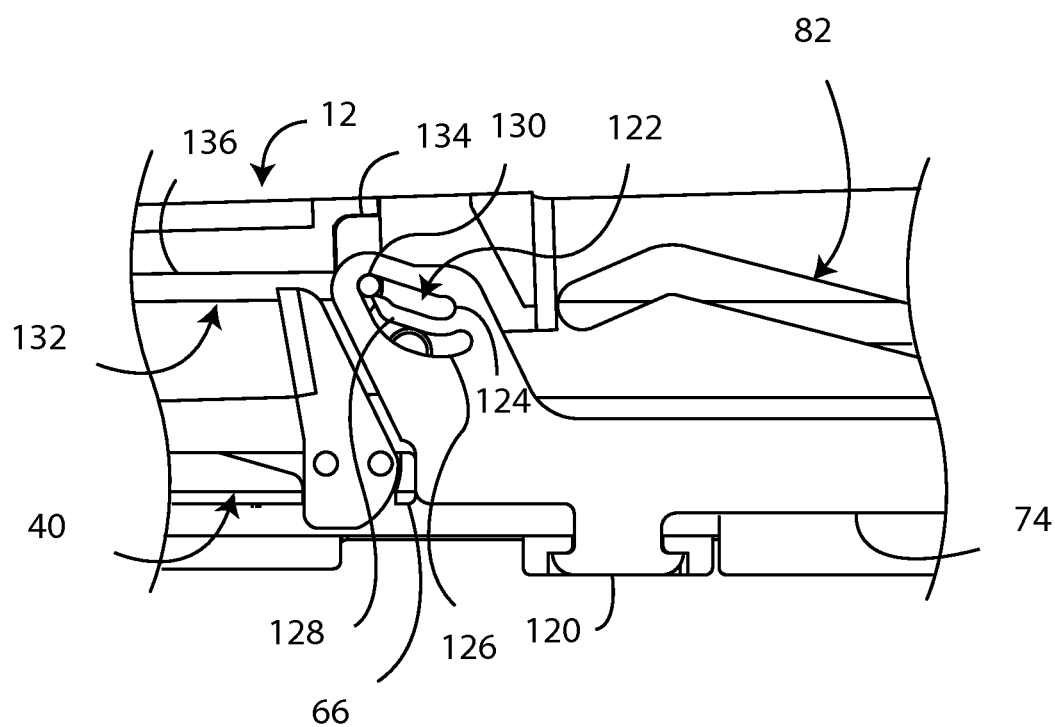
FIG. 17 is a detail cutaway side view of the end effector of FIG. 14 in a clamped position.

Referring to FIG. 17, the deployment strip 74 may be a thin, elongated structure that is fabricated from metal or any other suitable material. The deployment strip 74 may extend through the shaft 6 to the handle 8 of the surgical stapler 2. A foot 120 may extend downward from the deployment strip 74, at a location near or at the distal end of the deployment strip 74. The foot 120 is advantageously wider in the lateral direction than the deployment strip 74. A pin cutout 122 may be provided at or in proximity to the distal end of the deployment strip 74, at or near an upper end of the deployment strip 74. The pin cutout 122 may include a first channel 124 and a second channel 126 positioned below the first channel 124. The first channel 124 and second channel 126 may be shaped in substantially the same manner. A detent finger 128 separates the channels 124, 126 along the majority of their length. The detent finger 128 does not extend all the way to the distal end of the pin cutout 122, and is spaced apart from the distal end of the pin cutout 122 by a distance as least as great as the diameter of a cross pin 130. The cross pin 130 extends laterally through the pin cutout 122, but is not fixed to the deployment strip 74. Rather, the cross pin 130 is movable within the pin cutout 122, as is described in greater detail below. The anvil 12 includes two pin paths 132 defined laterally therein, spaced apart by a lateral distance at least as great as the lateral thickness of the deployment strip 74. The proximal end of each pin path 132 may be a pocket 134. The remainder of each pin path 132 may be a substantially linear travel slot 136 that is connected to and extends distally from the pocket 136. The cross pin 130 is thus slidable along the pin path 132, and movable within the pin cutout 122, while being trapped by and constrained within the pin path 132 and pin cutout 122.

Operation—Inserting Blue Cartridge

Prior to operation of the surgical stapler 2, the user chooses a cartridge 16, 30 for insertion into the jaw 14. Referring to FIGS. 2, 4, 5 and 15, the user may select a blue cartridge 16. The user then places the blue cartridge 16 into the jaw 14. The blue cartridge 16 may be friction-fit into the jaw 14, or may be locked affirmatively into the jaw 14 in any suitable manner. Referring in particular to FIG. 15, as the blue cartridge 16 is inserted into the jaw 14, each blue gap-setting feature 36 of the blue cartridge 16 comes into proximity with, and may contact, the shuttle 100. The shuttle 100 is biased distally, so each pivot pin 72 may be positioned against the proximal surface 110 of the center aperture 102 of the shuttle 100. The end effector 4 may be in the open position, so each pivot pin 72 is in a higher vertical position than when the end effector 4 is in the closed position. Thus, each pivot pin 72 may also be positioned against the upper surface 108 of the center aperture 102. As a result, before the blue cartridge 16 is loaded into the jaw 14, each pivot pin 72 may be positioned in the upper proximal corner of the center aperture 102. When the blue cartridge 16 is loaded, its blue gap-setting feature 36 is positioned far enough distally that it does not substantially engage the shuttle 100, leaving each pivot pin 72 in its original position in the upper proximal corner of the center aperture 102. Referring also to FIG. 4, when each pivot pin 72 is in the upper proximal corner of the center aperture 102, it may also be positioned at the upper end of the corresponding pivot pin slot 99 defined in the corresponding jaw wall 96.

Referring also to FIG. 17, after the blue cartridge 16 has been inserted into the jaw 14, the distal end of the deployment strip 74 is in proximity to, or in contact with, the fin 66 of the sled 40.

Operation—Inserting White Cartridge

Figure 18:
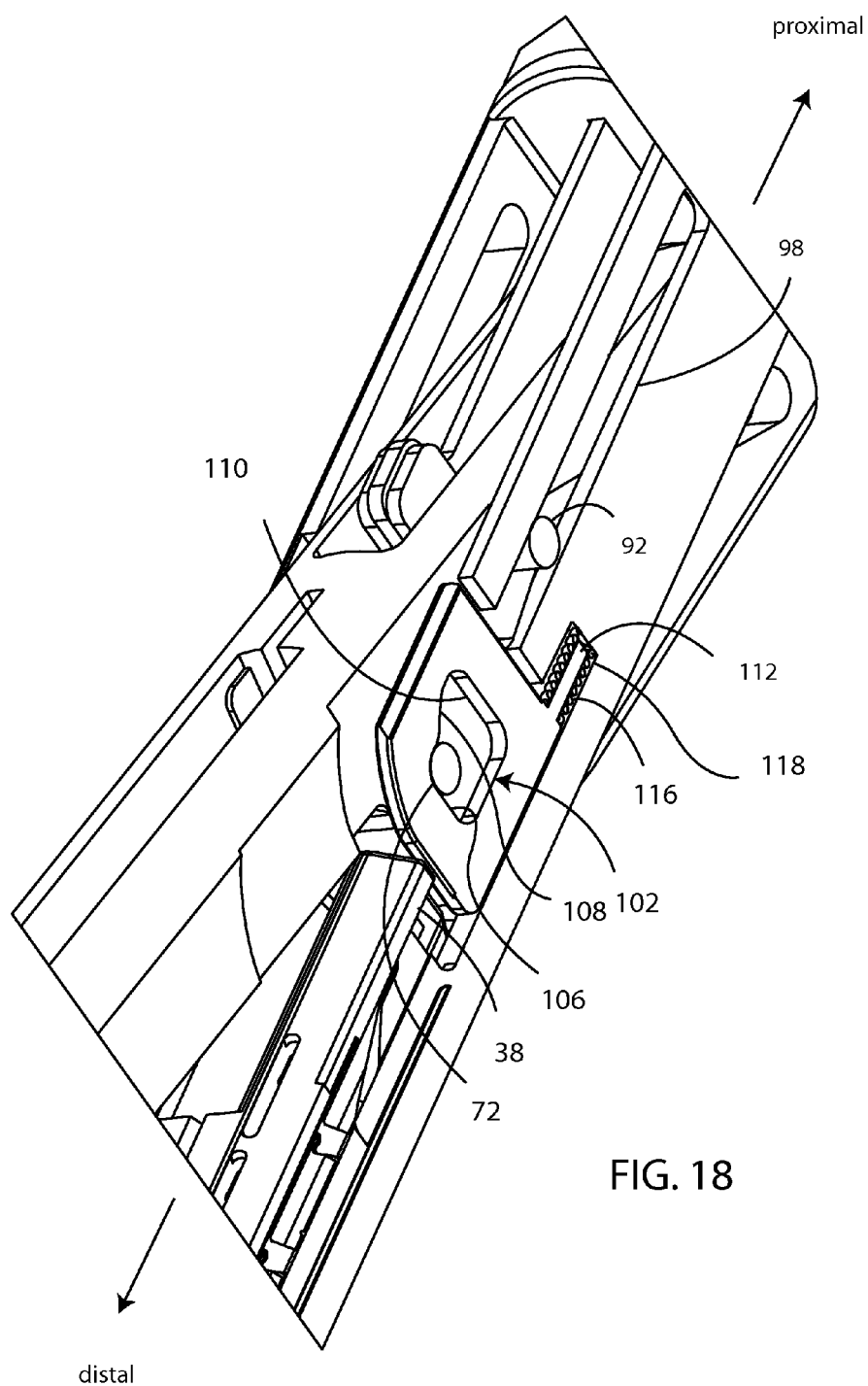
FIG. 18 is a detail cutaway perspective view of the end effector of FIG. 2, loaded with a white cartridge of FIG. 6.

Prior to operation of the surgical stapler 2, the user chooses a cartridge 16, 30 for insertion into the jaw 14. Referring to FIGS. 2, 6, 15 and 18, the user may select a white cartridge 30. The user then places the white cartridge 30 into the jaw 14. The white cartridge 30 may be friction-fit into the jaw 14, or may be locked affirmatively into the jaw 14 in any suitable manner. Referring in particular to FIG. 18, as the white cartridge 30 is inserted into the jaw 14, each white gap-setting feature 38 of the white cartridge 30 contacts the corresponding shuttle 100 and pushes the corresponding shuttle 100 in the proximal direction, overcoming the distal bias of the shuttles 100. As with the blue cartridge 16 described above, initially before loading the white cartridge 30 each pivot pin 72 is positioned in the upper proximal corner of the center aperture 102 of each shuttle 100. As each shuttle 100 moves proximally as a result of contact with the corresponding white gap-setting feature 38, each pivot pin 72 remains in substantially the same longitudinal position as a consequence of engagement between each pivot pin 72 and the corresponding pivot pin slot 99 defined in the corresponding jaw wall 96. That is, each pivot pin slot 99 substantially constrains the pivot pin 72 retained therein against longitudinal motion, while allowing vertical motion within the height defined by the pivot pin slot 99. Thus, as each shuttle 100 moves proximally, while the corresponding pivot pin 72 does not, contact between the upper surface 108 of the center aperture 102, which is sloped downward toward the distal direction, pushes the pivot pin 72 downward. When the white cartridge 30 has been fully inserted into the jaw 14, the white gap-setting features 38 have pushed each shuttle 100 proximally to a point at which each pivot pin 72 is located at the upper distal corner of the center aperture 102 of each shuttle 100. Because the distal surface 106 of each center aperture 102 is shorter in height than the proximal surface 110 of each center aperture 102, the upper distal corner of the center aperture 102 of each shuttle 100 is lower in height than the upper proximal corner of the center aperture 102 of each shuttle 100. Consequently, insertion of the white cartridge 30 into the jaw 14 has moved the pivot pin 72 lower. When each pivot pin 72 is in the upper distal corner of the center aperture 102, it may also be positioned at the lower end of the corresponding pivot pin slot 99 defined in the corresponding jaw wall 96.

As described above, the white gap-setting features 38 are located more proximal on the white cartridge 30 than the blue gap-setting features 36 are located on the blue cartridge 16. In this way, engagement between the white cartridge 30 and the shuttles 100 urges the shuttles 100 proximally a greater amount than engagement (or affirmative nonengagement) between the blue cartridge 16 and the shuttles 100. Thus, the clamp gap between the anvil 12 and any cartridge inserted into the jaw 14 is set by the longitudinal position of the shuttles 100, which controls the vertical position of the corresponding pivot pins 72. When the pivot pins 72 are set higher by the blue cartridge 16, the clamp gap is set larger to allow thicker tissue to be clamped between the anvil 12 and the blue cartridge 16, where the staples 18 held by the blue cartridge 16 are sized to staple tissue of that thickness. When the pivot pins 72 are set lower by the white cartridge 30, the clamp gap is set smaller to allow thinner tissue to be clamped between the anvil 12 and the white cartridge 30, where the staples 18 held by the white cartridge 30 are concomitantly smaller to staple thinner tissue. In this way, the clamp gap between the anvil 12 and each cartridge 16, 30 is automatically set to a distance that the staples 18 in the particular cartridge 16, 30 can be deployed across.

The shuttles 100 can be configured to accommodate additional sizes of cartridges, if desired. As one example, the end effector 4 may also accommodate a green cartridge, which holds larger staples than the blue cartridge 16. The term "green cartridge" is standard terminology for a cartridge that fires staples across a 0.050 inch clamp gap. If so, the shuttle 100 may be larger, and the upper surface 108 of the center aperture 102 of the shuttle 100 may be shaped differently to provide a stable position for the corresponding pivot pin 72 between the upper corners of that center aperture 102. For example, the upper surface 108 of the center aperture 102 of each shuttle 100 may be stepped such that the corresponding pivot pin 72 may reside at that step in a stable manner when the blue cartridge 16 is inserted into the end effector; if so, each pivot pin 72 may be positioned at the upper proximal corner of the center aperture 102 of each shuttle 100 when the green cartridge is inserted. Further, in such a situation, the white gap-setting features 38 are still located more proximal on the white cartridge 30 than the blue gap-setting features 36 are located on the blue cartridge 16; however, the blue gap-setting features 36 would be located proximally enough on the blue cartridge 16 to push the shuttles 100 proximally enough to allow the pivot pins 72 to seat in the steps in the center apertures 102, and the green gap-setting features would not substantially cause the shuttles 100 to move proximally.

When a cartridge 16, 30 is loaded onto the jaw 14, the end effector 4 is advantageously in an open position, such that the distal end of the anvil 12 is spaced apart from the jaw 14, and such that the anvil 12 is positioned at an angle relative to the jaw 14. In this way, there is sufficient clearance for the user to easily attach a cartridge 16, 30 to the jaw. In this open position, the clamp strip 90 may be positioned longitudinally relative to the anvil 12 such that the cam pin 92 is located at the proximal end of each first segment 84 of the cam path 82 defined in each leg 78 of the anvil 12. Alternately, the cam pin 92 may be positioned differently relative to the cam paths 82 defined in the legs 78 of the anvil 12.

Operation—Trocar Position

After a cartridge 16, 30 has been loaded onto the jaw 14, the surgical stapler 2 is ready for firing. The surgical stapler 2 may be used in a minimally-invasive procedure, where it is inserted through a trocar port into a patient's body. If so, it is advantageous to minimize the cross-sectional area of the end effector 4 during insertion into the patient in order to minimize the size of the trocar port that must be inserted into the patient's body. The minimum cross-sectional area position of the end effector 4 is defined as the "trocar position." In the trocar position, the end effector 4 advantageously has a cross-sectional area that is at least as small as that of the shaft 6, and additionally does not extend radially from the longitudinal centerline of the shaft 6 a distance greater than the outer surface of the shaft 6. As one example, the shaft 6 is five millimeters in diameter, such that the radius from the longitudinal centerline of the shaft 6 to the outer surface of the shaft 6 is 2.5 millimeters. In trocar position, the end effector 4 would assume a configuration such that all portions of the end effector 4 would be positioned radially within 2.5 millimeters of the longitudinal centerline of the shaft 6. As another example, the trocar position of the end effector 4 may result in the end effector 4 having a cross-sectional area that is larger than that of the shaft 6, or extending radially from the longitudinal centerline of the shaft 6 a distance greater than the outer surface of the shaft 6. The trocar position of the end effector 4 is advantageously a configuration of the end effector 4 in which the end effector 4 has a smaller cross-sectional area than a clamped configuration of the end effector 4. Further, in the trocar position, advantageously there is substantially no gap between the anvil 14 and the cartridge 16, 30 along a substantial length of the cartridge 16, 30. Optionally, a gap may still remain between the anvil 14 and the cartridge 16, 30 in trocar position.

Figure 19:
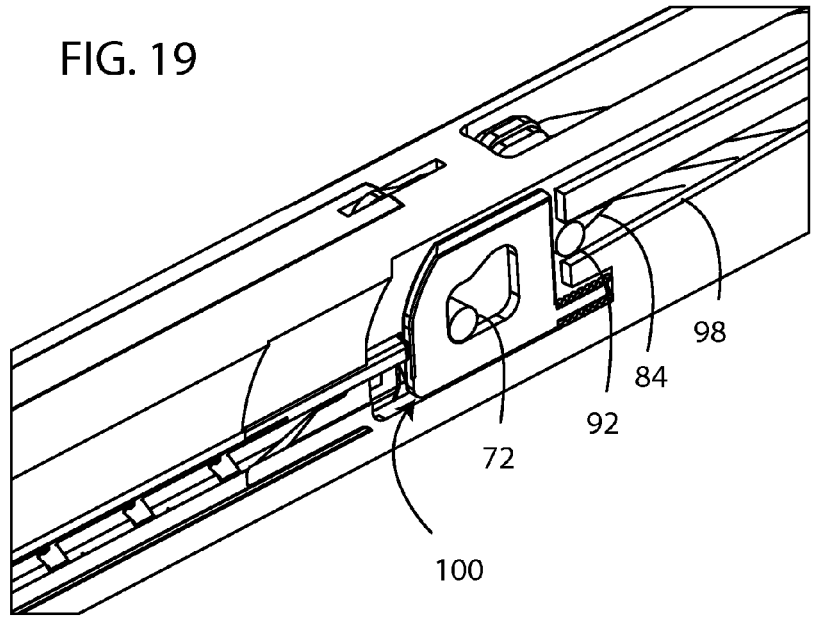
FIG. 19 is a cutaway perspective view of the end effector of FIG. 2 in trocar position, loaded with a white cartridge of FIG. 6.
Figure 20:
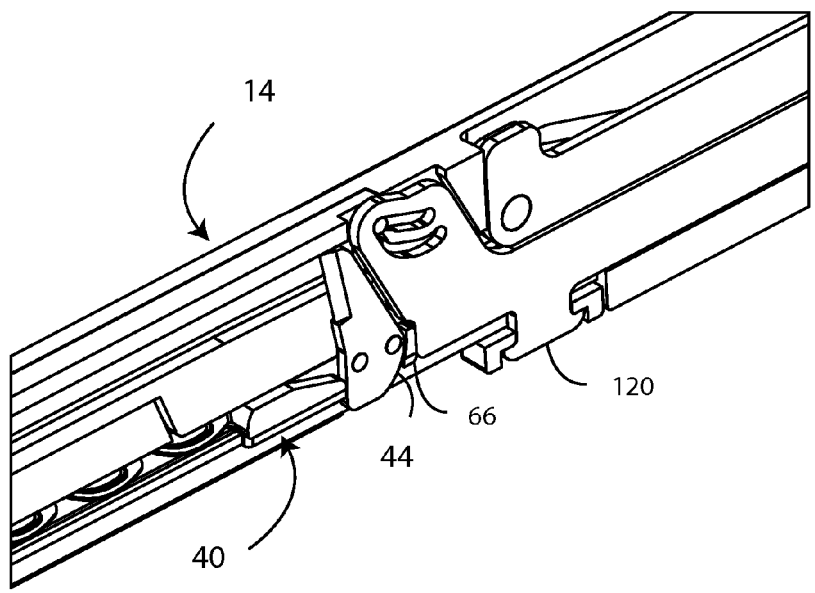
FIG. 20 is a cross-section view of the end effector of FIG. 2 in the trocar position, loaded with a white cartridge of FIG. 6.

The end effector 4 may be moved to the trocar position in any suitable manner. Referring also to FIGS. 19-20, as one example, to move the end effector 4 to the trocar position, the clamp strip 90 is advanced distally. The clamp strip 90 may be advanced distally in any suitable manner, such as by a force transmitted from the handle 8. As the clamp strip 90 advances distally, the cam pin 92 fixed to the clamp strip 90 advances distally as well. As the cam pin 92 advances distally, the cam pin 92 moves distally within each cam path 82 defined in each leg 78 of the anvil 12. Distal motion of the cam pin 92 moves the cam pin 92 within the first segment 84 of each cam path 82, which is oriented downward in the distal direction. Further, the cam pin 92 is constrained to move linearly and longitudinally by the cam pin slots 98 defined in the jaw 14. Consequently, as the cam pin 92 moves distally within the cam pin slots 98, the orientation of the first segment 84 of each cam path 82 defined in the anvil 12 causes the cam pin 92 to push the anvil 12 downward at the point of contact between the cam pin 92 and the anvil 12. As the anvil 12 is pushed downward, each pivot pin 72 is pushed downward within the center aperture 102 of the corresponding shuttle 100. Each pivot pin 72 may be pushed downward until it encounters the lower surface 104 of the center aperture 102. Alternately, at least one pivot pin 72 does not move downward a sufficient amount to encounter the lower surface 104 of the center aperture 102. Thus, when the end effector 4 is in the trocar position, each pivot pin 72 may be positioned in the lower distal corner of the center aperture 102 of each shuttle 100.

Referring also to FIG. 21, the anvil 12 may include a tissue stop 138 extending downward therefrom, at a location distal to the pivot pins 72. Referring also to FIG. 10, as the end effector 4 moves from the open position to the trocar position, the anvil 12 moves downward relative to the cartridge 16, 30 and the jaw 14. As the anvil 12 moves downward, the tissue stop 138 moves downward as well. As the tissue stop 138 continues to move downward, the tissue stop 138 may enter a space 140 defined in the proximal end of the cartridge 16, 30, where the space 140 is present to accommodate the tissue stop 138. As the tissue stop 138 continues to move downward, the tissue stop 138 encounters, and begins to exert a downward force upon, at least one flip pin 62 attached to the knife 44. The tissue stop 138 may be longitudinally bisected by a slot 142 that is at least as wide as the knife 44, such that a portion of the knife 44 can be received in the slot 142 as the tissue stop 138 continues to move downward. Because the flip pins 62 are located proximal to the pivot axle 58 of the knife 44, and the pivot axle 58 is fixed relative to the sled 40, the downward force exerted by the tissue stop 138 on the flip pins 62 flips the knife 44 up to a cutting position by rotating the flip pins 62 downward and proximally. The flip pins 62 may continue their rotation until encountering a surface of the sled 40, where that encounter prevents further rotation.

After the end effector 4 has been inserted into the patient, it is returned to the open position. The end effector 4 may be opened after it has been moved to the surgical space, or may be opened upon entry into the patient, at the discretion of the user. As can also been seen in FIG. 21, the anvil 12 pivots about a point substantially distal to its proximal end. The longitudinal distance between the proximal end of the anvil 12 and the point at which the anvil 12 pivots relative to the jaw 14 may be at least as long as the cam pin slots 98 defined in the jaw 14. The pivot pins 72 may be positioned substantially one-quarter of the length of the anvil 12 distally from the proximal end of the anvil 12. Further, in the open position, the legs 78 of the proximal end of the anvil 12 may protrude beneath the bottom of the jaw 14. An anvil aperture 158 may be defined through the lower surface of the jaw 14 in order to allow the proximal end of the anvil 12 to move therethrough and reach a position underneath the bottom of the jaw. In order to return the end effector 4 from the trocar position to the open position, the clamp strip 90 may be moved proximally, substantially to the position it had occupied when the cartridge 16, 30 was loaded onto the jaw 14. As a result, the clamp pin 92 moves proximally within each of the cam pin slots 98 in the jaw, and proximally within the cam paths 82 defined in the anvil 14. The consequence of this motion is substantially the reverse of the previous distal motion of the clamp pin 92 within the cam pin slots 98 and cam paths 82. As the cam pin 92 moves proximally within the cam pin slots 98, the orientation of the first segment 84 of each cam path 82 defined in the anvil 12 causes the cam pin 92 to pull the anvil 12 upward at the point of contact between the cam pin 92 and the anvil 12. As the anvil 12 is pulled upward, each pivot pin 72 is pushed downward within the center aperture 102 of the corresponding shuttle 100. Each pivot pin 72 may be pulled upward until it encounters the upper surface 108 of the center aperture 102. Alternately, at least one pivot pin 72 does not move upward a sufficient amount to encounter the upper surface 108 of the center aperture 102. Thus, when the end effector 4 is in the open position, each pivot pin 72 may be positioned in the upper distal corner of the center aperture 102 of each shuttle 100, in the position it had previously occupied when the end effector 4 was in the open position during loading of the cartridge 16, 30.

When the end effector 4 returns to the open position, the knife 44 remains in the flipped-up position, and is ready to cut tissue. The knife 44 remains in the flipped-up position because no force acts upon it to push it back to its down position. The pivot axle 58, and/or other portion of the knife, may be configured to have a small degree of frictional resistance to motion, in order to prevent the knife 44 from moving out of the flipped-up position as a result of the action of gravity or as a result of the user changing the orientation of the end effector 4. A detent or other mechanism or structure may instead be used to ensure that the knife remains in the flipped-up position during the transition of the end effector 4 from the trocar position to the open position.

Operation—Clamping

The user then places the end effector 4 about tissue to be treated, such that tissue is positioned between the anvil 12 and the cartridge 16, 30. Once the user is satisfied with the position of the end effector 4 relative to tissue, the user may clamp the end effector. Referring also to FIG. 22, as one example, in order to move from the open position to a clamped position, the clamp strip 90 is moved proximally. The clamp strip 90 may be retracted proximally in any suitable manner, such as by a force transmitted from the handle 8. As the clamp strip 90 retracts proximally, the cam pin 92 fixed to the clamp strip 90 retracts proximally as well. As the cam pin 92 retracts proximally, the cam pin 92 moves proximally within each cam path 82 defined in each leg 78 of the anvil 12. Proximal motion of the cam pin 92 moves the cam pin 92 within the second segment 86 of each cam path 82, which is oriented downward in the proximal direction. Further, the cam pin 92 is constrained to move linearly and longitudinally by the cam pin slots 98 defined in the jaw 14. Consequently, as the cam pin 92 moves proximally within the cam pin slots 98, the orientation of the second segment 86 of each cam path 82 defined in the anvil 12 causes the cam pin 92 to lift the anvil 12 upward at the point of contact between the cam pin 92 and the anvil 12. As the proximal end of the anvil 12 is lifted upward, each pivot pin 72 experiences a force that urges that pivot pin 72 upward. However, each pivot pin 72 is already positioned against the upper surface 108 of the center aperture 102 of the corresponding shuttle 100, whether in the upper, distal corner of the center aperture 102 where the white cartridge 30 is loaded, or in the upper, proximal corner of the center aperture 102 where the blue cartridge 16 is loaded. Consequently, as the proximal end of the anvil 12 is lifted by the cam pin 92, the shuttles 100 provide a downward constraint on the anvil 12. As a result, the anvil 12 pivots about the pivot pins 72 as the proximal end of the anvil 12 is lifted. Thus, referring to FIG. 22, if no tissue were positioned between the anvil 12 and the cartridge 16, 30, then the anvil 12 would be angled forward, such that the distal end of the anvil 12 would be closer to the cartridge 16, 30 than the portion of the anvil 12 adjacent to the pivot pins 72. This angle of the anvil 12 compensates for deflection of the anvil 12 under tissue loading. Deflection of a cantilever such as the anvil 12 increases with distance from the pivot point, such that angling the anvil 12 forward as shown in FIG. 22 results in an anvil 12 that is substantially parallel to the cartridge 16, 30 when tissue is present between the anvil 12 and the cartridge 16, 30.

The end effector 4 has reached the clamped position after the cam pin 92 has reached the proximal end of the second segment 86 of the cam paths 82 in the anvil 12, such that it cannot move further proximally. Alternately, the tissue thickness may be such that the cam pin 92 only moves partially along the second segment 86 before it can no longer advance, due to the force needed to further compress the tissue being greater than the force that can be exerted by the cam pin 92. After the tissue has been clamped, the surgical stapler 2 is ready to fire. Optionally, a locking feature may be provided in the handle 8 or elsewhere to ensure that the end effector 4 remains locked. Such locking may be performed at the discretion of the user, or automatically, such as by immobilizing the clamp strip 90 to prevent it from moving after the end effector 4 reaches the clamped position. In the clamped position, the presence of a clamp gap between the anvil 12 and the cartridge 16, 30 means that the cross-sectional area of the end effector 4 in the clamped position is greater than the cross-sectional area of the end effector 4 in the trocar position.

Operation—Blue Cartridge

For the blue cartridge 16, the end effector 4 has reached the clamped position after the cam pin 92 has reached the proximal end of the second segment 86 of the cam paths 82 in the anvil 12, such that it cannot move further proximally. Alternately, the cam pin 92 may only move partially along the second segment 86 before it can no longer advance, due to the force needed to further compress the tissue being greater than the force that can be exerted by the cam pin 92. After the tissue has been clamped, the surgical stapler 2 is ready to fire. Optionally, a locking feature may be provided in the handle 8 or elsewhere to ensure that the end effector 4 remains locked. Such locking may be performed at the discretion of the user, or automatically, such as by immobilizing the clamp strip 90 to prevent it from moving after the end effector 4 reaches the clamped position.

Figure 23:
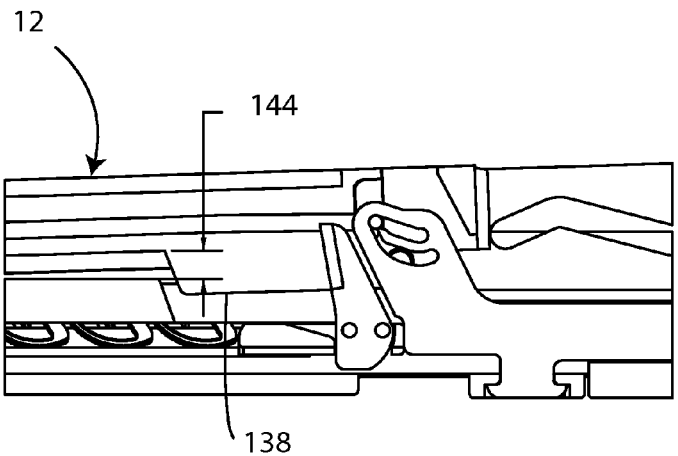
FIG. 23 is a detail cutaway view of the end effector of FIG. 2 showing the clamp gap.

The staples 18 in the blue cartridge 16 are designed to operate most efficaciously when deployed across a clamp gap of generally 0.035 inches. Referring also to FIG. 23, the clamp gap 144 is defined as the space between the anvil 12 and the cartridge 16, 30, measured longitudinally at the distal end of the tissue stop 138. The location of measurement is specified due to the fact that the anvil 12 angles downward in the distal direction in the absence of tissue, as described above. Thus, when the blue cartridge 16 is positioned in the jaw 14, the clamp gap 144 is advantageously substantially 0.035 inches. The clamp gap 144 is controlled by the position of the shuttles 100. As set forth above, when the blue cartridge 14 is loaded into the jaw 14, each pivot pin 72 is located in the upper, proximal corner of the center aperture 102 of the corresponding shuttle 100. This height of the pivot pins 72 results in an angle of the anvil 12 downward in the distal direction such that the clamp gap 144 measured at the distal end of the tissue stop 138, which is distal to the pivot pins 72, is the appropriate amount of 0.035 inches for a blue cartridge 16. At that height, each pivot pin 72 may be located at or near the upper end of the corresponding pivot pin slot 99 in the jaw 14. Alternately, at least one pivot pin 72 may be spaced downwardly from the upper end of the corresponding pivot pin slot 99 in the jaw 14.

Referring also to FIG. 17, in order to deploy staples 18 from the blue cartridge 16, the deployment strip 74 is advanced distally. The cross pin 130, held by the detent finger 128, is advanced distally with the deployment strip 74. Due to the spacing between the anvil 12 and the blue cartridge 16 set by the shuttles 100, the cross pin 130 is at substantially the same height relative to the blue cartridge 16 as the travel slots 136. That is, the cross pin 130 is in vertical alignment with the travel slots 136. As a result, as the cross pin 130 advances distally, it slides into the travel slots 136, held by the detent finger 128.

Figure 8:
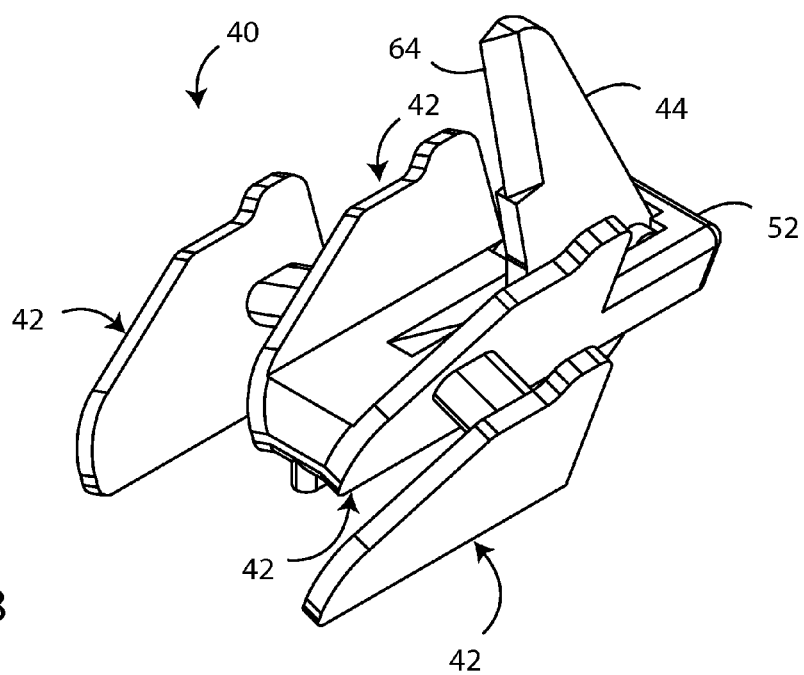
FIG. 8 is a perspective view of an exemplary sled assembly, with a knife in the up position.

Referring also to FIG. 8, in addition, as the deployment strip 74 advances distally, the deployment strip 74 contacts the fin 66 of the sled 40, and thereby pushes the sled 40 distally. As the sled 40 advances distally, the wedges 42 and knife 44 advance distally. Each wedge 42 contacts, deforms, and then shears from the feeder belt 20 one or more staples 18, in a linearly sequential manner. Each wedge 42 directly contacts one or more staples 18, without the need for an intermediate staple driver between the wedge 42 and any staple 18. Deformation of the staples 18 and subsequent breaking off of those staples 18 from the corresponding feeder belt 20 may be performed substantially as set forth in the Endocutter Document. The knife 44 may be positioned proximal to one or more wedges 42, such that staples 18 are sequentially deployed before the stapled tissue is cut by the blade 64 of the knife 44. Alternately, the knife 44 may be positioned differently on the sled 40 such that the blade 64 cuts tissue at a different time relative to stapling.

Figure 24:
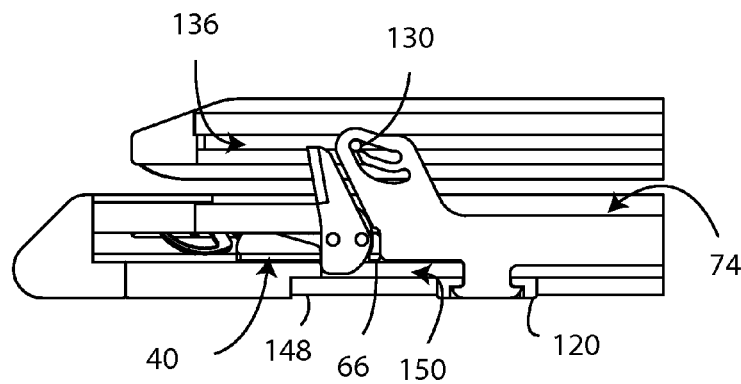
FIG. 24 is a detail cutaway side view of the end effector of FIG. 14 in a clamped position, loaded with a blue cartridge of FIG. 5, in a stage of deployment.

Referring also to FIG. 24, as the deployment strip 74 advances, the cross pin 130 continues to advance distally along the travel slots 136. Additionally, the foot 120, which is attached to the deployment strip 74, advances distally with the deployment strip 74. The foot 120 may slide along a channel 148 defined in an undersurface of the jaw 14, such that the bottom of the foot 120 is substantially flush with the undersurface of the jaw 14, or may simply slide along the undersurface of the jaw 14. In either case, the foot 120 travels distally at a height that is substantially the same along the entire distance of travel of the deployment strip 74. The combination of the cross pin 130 held in the travel slots 136 and by the deployment strip 74, and the foot 120 extending from the deployment strip 74 and sliding along a defined surface on the jaw 14, provides additional localized clamping between the cross pin 130 and the foot 120 as the deployment strip 74 advances. Because the foot 120 is constrained to travel along a longitudinal path defined by the channel 148 or the underside of the jaw 14, in order for the cross pin 130 to continue moving forward into the travel slots 136, the cross pin 130 must exert a downward force against the lower surfaces of the travel slots 136, locally increasing compression as necessary in order to counteract any bending of the anvil 12 as a result of compression of tissue between the anvil 12 and the blue cartridge 16.

Figure 25:
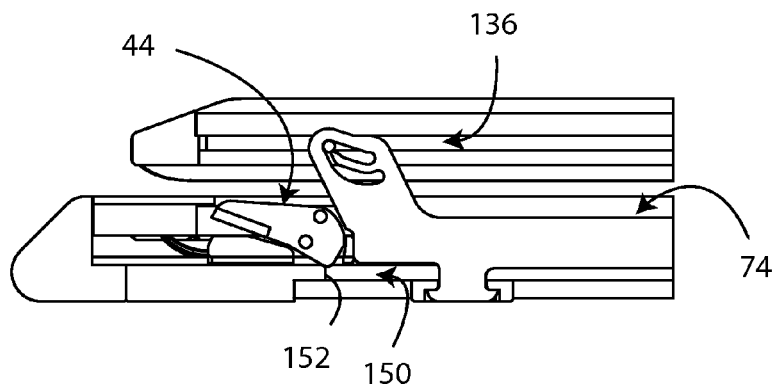
FIG. 25 is a detail cutaway side view of the end effector of FIG. 24, in a further stage of deployment.
Figure 26:
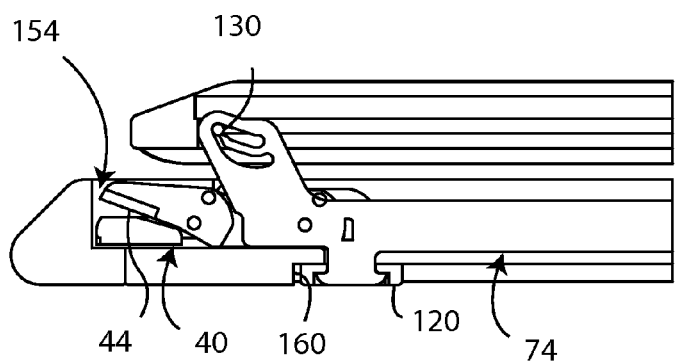
FIG. 26 is a detail cutaway side view of the end effector of FIG. 25, in a further stage of deployment.

Referring also to FIG. 25, as the deployment strip 74 nears the end of its travel distally, the knife 44 begins to rotate back downward to its down position. Previously, the bottom of the knife 44 slid along the knife slot 150 defined in an undersurface of the jaw 14. The knife slot 150 may be defined completely through the undersurface of the jaw 14, or may simply be a recess within the jaw 14. As the deployment strip 74 nears the end of its travel, the bottom of the knife 44 contacts the distal end 152 of the knife slot 150. This contact occurs below the pivot axle 58 of the knife 44, thereby causing the knife 44 to rotate about the pivot axle 58 distally and downwardly. As the knife 44 rotates down and distally, it makes a final cut to tissue with a "karate chop" motion, if tissue is located at that position relative to the knife 44. Referring also to FIG. 26, the deployment strip 74 continues to advance, pushing the sled 40 and the knife 44 distally. The knife 44 has reached the down position, and is located within a parking space 154 defined within, and at or near the distal end of, the blue cartridge 16. In this way, after use the knife 44 is securely stowed in a manner in which it cannot cause inadvertent injury to the user. Advantageously, the sled 40 is frictionally locked into engagement, or otherwise affirmatively locked into engagement, with the parking space 154 such that the knife 44 is securely held inside the parking space 154. The deployment strip 74 may continue advancing distally until the cross pin 130 encounters the distal end of the travel slots 136, which stops further distal motion of the deployment strip 74. Alternately, or in addition, the foot 120 may encounter a foot stop 160 defined in the jaw 14, such as at the distal end of the channel 148, such that contact between the foot stop 160 and the foot 120 prevents further distal motion of the deployment strip 74. Alternately, the deployment strip 74 may be controlled by the handle 8 or in another manner to travel through a stroke and stop at a location that is defined other than by encountering a physical stop point that provides a barrier to further distal motion.

The tissue between the anvil 12 and blue cartridge 16 has now been stapled by staples 18 and divided by the knife 44. The deployment strip 74 is then moved proximally. The sled 40 is held in the parking space 154, and remains in the parking space 154 as the deployment strip 74 moves proximally to its initial location. The cross pin 130 moves proximally out of the travel slots 136 and into the pockets 134. At that time, the cross pin 130 and foot 120 no longer provide additional clamping to the end effector 4. The end effector 4 can then be unclamped in the reverse of the manner in which it was clamped. The clamp strip 90 is moved distally, and the concomitant distal motion of the cam pin 92 moves the cam pin 92 distally within the second segment 86 of each cam path 82, which is oriented downward in the proximal direction. Further, the cam pin 92 is constrained to move linearly and longitudinally by the cam pin slots 98 defined in the jaw 14. Consequently, as the cam pin 92 moves distally within the cam pin slots 98, the orientation of the second segment 86 of each cam path 82 defined in the anvil 12 causes the cam pin 92 to push the anvil 12 downward at the point of contact between the cam pin 92 and the anvil 12. As the proximal end of the anvil 12 is pushed downward, each pivot pin 72 experiences a force that urges that pivot pin 72 upward. The end effector 4 thus returns to the open position.

After the end effector 4 has been opened, the user can remove the spent blue cartridge 16. The sled 40, including the knife 44, is part of the spent blue cartridge 16, and is disposable along with the remainder of the spent blue cartridge 16. At that time, if the user wishes to perform further treatment of the patient, the user can insert a blue cartridge 16 or a white cartridge 30 into the jaw 14 of the end effector 4.

Operation—White Cartridge

Figure 27:
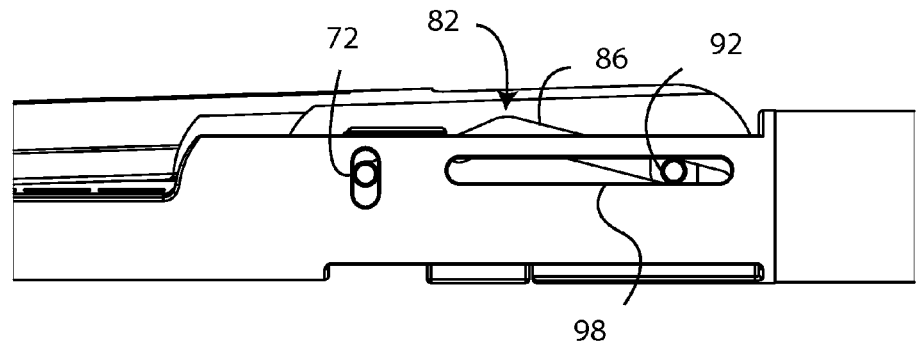
FIG. 27 is a side view of the end effector of FIG. 14 in a clamped position, loaded with a white cartridge of FIG. 6.

Referring also to FIG. 27, the cam pin 92 need not travel proximally as far to clamp a white cartridge 30 as a blue cartridge 16. This is because the tissue to be clamped when a white cartridge 30 is used is thinner than the tissue clamped when a blue cartridge 16 is used, so that less force is necessary to effectuate clamping. The cam pin 92 need not travel completely to the proximal end of the second segment 86 of the cam paths 82 in the anvil 12, or the proximal ends of the cam pin slots 98 in the jaw 14, in order for the end effector to reach the clamped position when a white cartridge 30 is in place in the jaw 14. Alternately, the cam pin 92 may move completely the proximal end of the second segment 86 of the cam paths 82 in the anvil 12, and/or the proximal ends of the cam pin slots 98 in the jaw 14, to effectuate clamping where a white cartridge 30 is loaded into the jaw 14. As another example, it may be desirable for the cam pin 92 to move a fixed amount proximally each time clamping is performed in order to simplify construction and operation of the surgical stapler 2. If so, a pre-loaded compression spring (not shown) may be connected to the clamp strip 90, where the compression loaded is equal to the desired maximum tissue pressure to be exerted by the end effector 4 in clamped position. Further motion of the cam pin 92 proximally, after that force has been reached, is taken up by the spring, which absorbs the "extra" stroke of the clamp strip 90. In this way, the end effector 4 is clamped to a predetermined force, rather than clamped to the position of the cam pin 92 within the end effector 4. After the tissue has been clamped, the surgical stapler 2 is ready to fire. Optionally, a locking feature may be provided in the handle 8 or elsewhere to ensure that the end effector 4 remains locked. Such locking may be performed at the discretion of the user, or automatically, such as by immobilizing the clamp strip 90 to prevent it from moving after the end effector 4 reaches the clamped position.

Referring also to FIG. 23, the staples 18 in the white cartridge 30 are designed to operate most efficaciously when deployed across a clamp gap 144 of generally 0.020 inch. The clamp gap 144 is controlled by the position of the shuttles 100. As set forth above, when the white cartridge 30 is loaded into the jaw 14, each pivot pin 72 is located in the upper, distal corner of the center aperture 102 of the corresponding shuttle 100. This height of the pivot pins 72 results in an angle of the anvil 12 downward in the distal direction such that the clamp gap 144 measured at the distal end of the tissue stop 138, which is distal to the pivot pins 72, is the appropriate amount of 0.020 inches for a blue cartridge 16. In this way, the cartridges 16, 30 each set a discrete clamp gap 144, such that the end effector 4 is configured to provide at least two discrete clamp gaps 144. Further, that height of each pivot pin 72 may place it substantially in the middle of the corresponding pivot pin slot 99. Alternately, at least one pivot pin 72 may be positioned against the lower end of the pivot pin slot 99 in the clamped position. In the clamped position, the height of each pivot pin 72 when the white cartridge 30 is used is lower than the height of each pivot pin 72 when the blue cartridge 16 is used.

Figure 28:
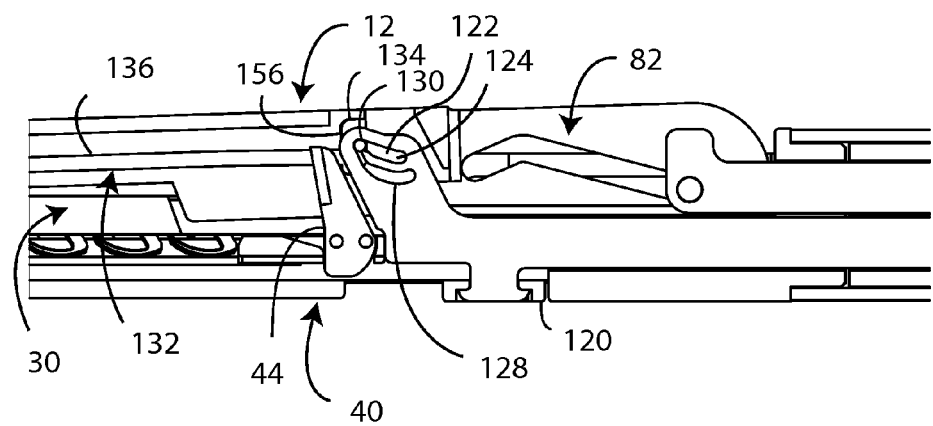
FIG. 28 is a detail cutaway side view of the end effector of FIG. 14 in a clamped position, loaded with a white cartridge of FIG. 6.
Figure 29:
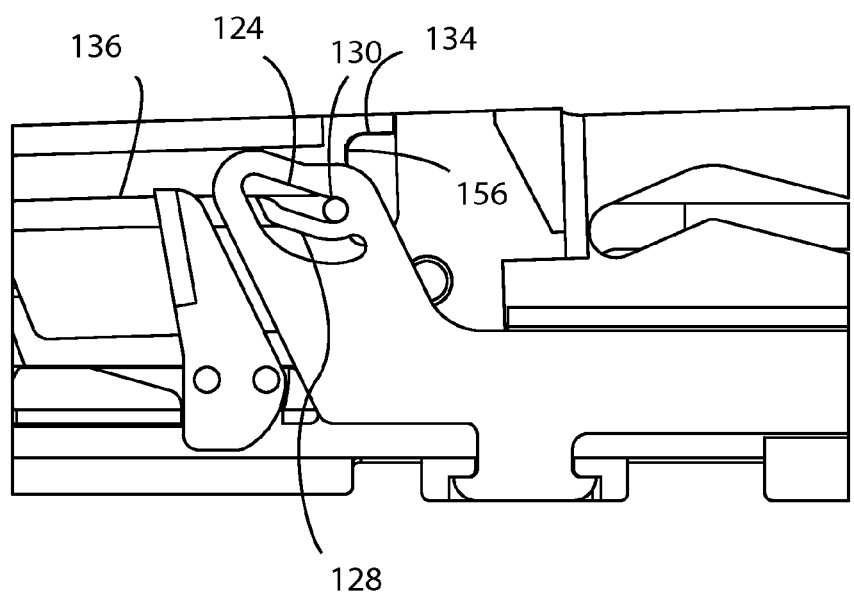
FIG. 29 is a detail cutaway side view of the end effector of FIG. 14 in a firing position, loaded with a white cartridge of FIG. 6.

Referring also to FIG. 28, in order to deploy staples 18 from the white cartridge 30, the deployment strip 74 is advanced distally. The cross pin 130, held by the detent finger 128, is advanced distally with the deployment strip 74. Due to the spacing between the anvil 12 and the white cartridge 30 set by the shuttles 100, the cross pin 130 is located higher relative to the white cartridge 30 as the travel slots 136. That is, the cross pin 130 is out of vertical alignment with the travel slots 136. As a result, as the cross pin 130 advances distally, it encounters the front wall 156 of each pocket 134. Continued motion distally of the deployment strip 74 thereby forces the cross pin 130 against the front wall 156, consequently forcing the cross pin 130 off of the detent finger 128 and into the first channel 124. As the deployment strip 74 continues to move distally, the cross pin 130 continues to slide into the first channel 124. The first channel 124 is oriented longitudinally, and downward in the longitudinal direction. Thus, the cross pin 130 continues to slide relative to the first channel 124 until the cross pin 130 is vertically aligned with the travel slots 136. At that time, further distal motion of the deployment strip 74 urges the cross pin 130 into the travel slots 136. Referring also to FIG. 29, the first channel 124 may be configured such that the proximal end of the first channel 124 is at substantially the same height relative to the white cartridge 30 as the travel slots 136, such that the cross pin 130 is located at the proximal end of the first channel 124 when the cross pin 130 is vertically aligned with the travel slots 136. This ability of the cross pin 130 to change vertical height depending on the clamp gap 144 set by the inserted cartridge 16, 30 allows the end effector 4 to clamp effectively at two or more discrete clamp gaps 144.

Deployment of staples 18 from the white cartridge 30 is performed substantially as described above with regard to the blue cartridge 16, and in the Endocutter Document. Advancement of the deployment strip 74 pushes the sled 40 distally, which in turn deforms staples 18, breaks staples 18 from the corresponding feeder belt 20, and cuts the stapled tissue held between the anvil 12 and the white cartridge 30. Continued advancement of the deployment strip 74 completes a firing stroke, after which the knife 44 enters the parking space 154 at the distal end of the white cartridge 30. The deployment strip 74 may then be retracted proximally and the end effector 4 unclamped and returned to the open position, at which time the user can remove the spent white cartridge 30. The sled 40, including the knife 44, is part of the spent white cartridge 30, and is disposable along with the remainder of the spent white cartridge 30. If the user wishes to perform further treatment of the patient, the user can insert a blue cartridge 16 or a white cartridge 30 into the jaw 14 of the end effector 4.

Manual Clamp Gap Setting

As another example of the end effector 4, the clamp gap 144 optionally may be set manually, rather then automatically. By way of example, the shuttles 100 may be movable longitudinally as a result of manual intervention. A cable, rod, strip or other structure may extend from the shuttles 100 to the handle 8, such that the user can adjust the longitudinal position of the shuttles 100 by way of manual input to the handle 8. As another example, the longitudinal position of the shuttles 100 may be set by way of a switch, such as a slider, on the end effector 4 itself. Where the clamp gap 144 is set manually, the gap-setting features 36, 38 may be omitted from the cartridges 16, 30.

While the invention has been described in detail, it will be apparent to one skilled in the art that various changes and modifications can be made and equivalents employed, without departing from the present invention. It is to be understood that the invention is not limited to the details of construction, the arrangements of components, and/or the method set forth in the above description or illustrated in the drawings. Statements in the abstract of this document, and any summary statements in this document, are merely exemplary; they are not, and cannot be interpreted as, limiting the scope of the claims. Further, the figures are merely exemplary and not limiting. Topical headings and subheadings are for the convenience of the reader only. They should not and cannot be construed to have any substantive significance, meaning or interpretation, and should not and cannot be deemed to indicate that all of the information relating to any particular topic is to be found under or limited to any particular heading or subheading. Therefore, the invention is not to be restricted or limited except in accordance with the following claims and their legal equivalents.

What is claimed is:

1. A surgical apparatus for treating tissue, comprising:
   an anvil;
   a jaw pivotally connected to said anvil;
   a first cartridge detachably connected to said anvil, said first cartridge holding staples of a first size and including a first gap-setting feature defined in an exterior of the first cartridge, wherein a first clamp gap between said anvil and said first cartridge is set by said gap-setting feature; and
   at least one shuttle held by said jaw, wherein said shuttle is biased distally and slidable longitudinally, and wherein said shuttle is configured to engage said gap-setting feature when said first cartridge is inserted into said jaw.

2. The surgical apparatus of claim 1, further comprising a second cartridge detachably connected to said anvil, said second cartridge holding staples of a second size and including a second gap-setting feature defined in an exterior of the second cartridge, wherein a second clamp gap between said anvil and said second cartridge is set by said second gap-setting feature, and wherein said first clamp gap is different from said second clamp gap.

3. The surgical apparatus of claim 2, wherein said first gap-setting feature is located further proximal in the first cartridge than the second gap-setting feature is located in said second cartridge.

4. The surgical apparatus of claim 1, wherein said shuttle comprises a central aperture with a greater height at its proximal end than its distal end.

5. The surgical apparatus of claim 4, further comprising at least one pivot pin constrained within and movable within said central aperture of a corresponding said shuttle, wherein each said pivot pin interconnects said anvil and said jaw.

6. The surgical apparatus of claim 5, further comprising at least one pivot pin slot defined in said jaw within which a corresponding said pivot pin is slidable, wherein said pivot pin slot is substantially linear and oriented substantially vertically.

7. The surgical apparatus of claim 6, wherein engagement between each said gap-setting feature and a corresponding said shuttle pushes said shuttle proximally, such that each corresponding said pivot pin moves to the upper distal corner of said central aperture of said shuttle.

8. The surgical apparatus of claim 1, further comprising a deployment slide slidable longitudinally into and within said first cartridge, wherein said deployment slide includes a foot slidable along an outer surface of said jaw, a pin cutout having a first channel defined therein; a detent finger under said first channel, and a cross pin held within said pin cutout, wherein said cross pin is movable between a first position in which said cross pin is held by said detent finger and a second position in which said cross pin is held within said first channel.

9. The surgical apparatus of claim 8, further comprising a sled that includes a plurality of wedges and a rotatable knife, wherein said deployment slide is positioned proximal to said sled such that distal sliding of said deployment slide pushes said sled distally; wherein distal motion of said sled causes said wedges to contact said staples directly to deploy said staples, and additionally causes said knife to cut tissue.

10. The surgical apparatus of claim 1, further comprising:
    a clamp slide slidable longitudinally within said jaw;
    a clamp pin fixed to said clamp side;
    at least one cam path defined in said anvil, within which said cam pin is slidable; and
    at least one cam pin slide defined in said jaw, within which said cam pin is slidable;
    wherein longitudinal motion of said clamp pin in a first direction causes said anvil to move from an open position to a closed position.

11. The surgical apparatus of claim 10, wherein each said cam pin slide is substantially linear and oriented substantially longitudinally.

12. The surgical apparatus of claim 10, wherein said anvil includes two laterally-spaced legs, each of which includes one said cam path defined therein.

13. The surgical apparatus of claim 10, wherein longitudinal motion of said clamp pin in a second direction causes said anvil to move from an open position to a trocar position.

* * * * *